United States Patent
Schaetzer et al.

(10) Patent No.: US 6,599,861 B2
(45) Date of Patent: Jul. 29, 2003

(54) HERBICIDES

(75) Inventors: Jürgen Schaetzer, Rheinfelden (DE); Alain De Mesmaeker, Kaenerkinden (CH); Shy-Fuh Lee, Sunnyvale, CA (US)

(73) Assignee: Syngenta Participations AG, Basel (CH)

( * ) Notice: Subject to any disclaimer, the term of this patent is extended or adjusted under 35 U.S.C. 154(b) by 5 days.

(21) Appl. No.: 09/886,896

(22) Filed: Jun. 21, 2001

(65) Prior Publication Data

US 2002/0165096 A1 Nov. 7, 2002

Related U.S. Application Data

(63) Continuation of application No. PCT/EP99/10128, filed on Dec. 20, 1999.

(30) Foreign Application Priority Data

Dec. 21, 1998 (CH) .............................................. 2521/98

(51) Int. Cl.[7] ........................ A01N 35/06; A01N 41/10; C07C 317/24
(52) U.S. Cl. ...................... 504/288; 504/292; 504/310; 504/313; 504/326; 504/333; 549/23; 549/397; 558/415; 560/256; 564/374; 564/384; 568/31; 568/42; 568/327
(58) Field of Search ................... 549/23, 397; 558/415; 560/256; 568/31.42, 327; 504/288, 292, 310, 313, 326, 333; 564/374, 384

(56) References Cited

U.S. PATENT DOCUMENTS

| 5,094,685 A | 3/1992 | Baba et al. ................... 71/103 |
|---|---|---|
| 5,336,662 A | 8/1994 | Lee .............................. 504/223 |
| 5,565,410 A | 10/1996 | Lee .............................. 504/223 |
| 5,608,101 A | 3/1997 | Lee et al. ...................... 560/11 |
| 5,700,762 A | 12/1997 | Lee et al. ..................... 504/292 |
| 5,801,120 A | 9/1998 | Lee et al. .................... 504/236 |
| 6,376,429 B1 * | 4/2002 | Van Almsick et al. ...... 504/271 |

FOREIGN PATENT DOCUMENTS

| EP | 0 282 944 A2 | 9/1988 |
| EP | 0 338 992 A2 | 10/1989 |
| EP | 0 394 889 A2 | 10/1990 |

OTHER PUBLICATIONS

Van Almsick et al. Chemical Abstracts, vol. 132:264966, 2000.*
Auler et al., Chemical Abstracts, 2002:832539, 2002.*

* cited by examiner

Primary Examiner—Richard L. Raymond
(74) Attorney, Agent, or Firm—Thomas Hamilton

(57) ABSTRACT

Compounds of formula I (I)

wherein the substituents are defined as in claim 1, as well as the agronomically acceptable salts, isomers and enantiomers of these compounds, as well as the agronomically acceptable salts/N-oxides/isomers/enantiomers of these compounds, are eminently suitable for use as herbicides.

8 Claims, No Drawings

HERBICIDES

This application is a continuation of International Application No. PCT/EP99/10128, filed Dec. 20, 1999, the contents of which are incorporated herein by reference.

The present invention relates to novel herbicidally active benzoyl derivatives, to processes for their preparation, to compositions comprising said compounds, and to the use thereof for controlling weeds, in particular in crops of cultivated plants or for inhibiting plant growth.

Benzoyl derivatives with herbicidal activity are described for example in U.S. Pat. No. 5,094,685. Now, novel benzoyl derivatives with herbicidal and growth-inhibiting properties have been found.

The objects of the present invention are thus compounds of formula I

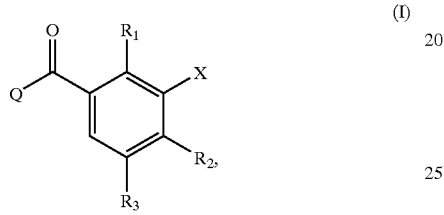

(I)

wherein

X is $L_1$-$Y_1$-$R_4$, $L_2$-$Y_2$-$L_3$-$Y_3$-$R_5$ or $L_4$-$Y_4$-$L_5$-$Y_5$-$L_6$-$Y_6$-$R_6$;

$L_1$, $L_2$, $L_3$, $L_4$, $L_5$, $L_6$, independently of one another, signify $C_1$-$C_6$-alkylene, which may be substituted by $C_1$-$C_4$-alkyl, halogen, $C_1$-$C_4$-alkoxy, $C_2$-$C_6$-alkenyl or $C_2$-$C_6$-alkynyl; or $C_3$-$C_6$-alkenylene, which may be substituted by $C_1$-$C_4$-alkyl, halogen, $C_1$-$C_4$-alkoxy, $C_2$-$C_6$-alkenyl or $C_2$-$C_6$-alkynyl; or $C_3$-$C_6$-alkynylene, which may be substituted by $C_1$-$C_4$-alkyl, halogen, $C_1$-$C_4$-alkoxy, $C_2$-$C_6$-alkenyl or $C_2$-$C_6$-alkynyl;

$Y_1$, $Y_3$, $Y_6$, independently of one another, signify oxygen, sulphur, SO, $SO_2$, $NR_7$, OC(O), $NR_8SO_2$ or $OSO_2$;

$Y_2$, $Y_4$, $Y_5$, independently of one another, signify oxygen, sulphur, SO, $SO_2$, $NR_9$, OC(O) or $NR_{10}SO_2$;

$R_7$, $R_8$, $R_9$ and $R_{10}$, independently of one another, signify hydrogen or $C_1$-$C_6$-alkyl;

$R_1$ and $R_2$, independently of one another, signify halogen, cyano, nitro, amino, $C_1$-$C_6$-alkyl, $C_1$-$C_6$-alkoxy, $C_1$-$C_4$-alkoxy-$C_1$-$C_4$-alkyl, $C_1$-$C_6$-halogenalkyl, $C_2$-$C_6$-alkenyl, $C_2$-$C_6$-alkynyl, $C_1$-$C_6$-alkoxycarbonyl, $C_1$-$C_6$-alkylcarbonyl, $C_1$-$C_6$-alkylthio, $C_1$-$C_6$-alkylsulphinyl, $C_1$-$C_6$-alkylsulphonyl, $C_1$-$C_6$-dialkylaminosulphonyl, $C_1$-$C_6$-alkylaminosulphonyl, $C_1$-$C_4$-alkylsulphonylamino, $C_1$-$C_6$-halogenalkoxy, $OSO_2$-$C_1$-$C_4$-alkyl, $C_1$-$C_6$-halogenalkylthio, $C_1$-$C_6$-halogenalkylsulphinyl, $C_1$-$C_6$-halogenalkylsulphonyl, phenylthio, phenylsulphinyl or phenylsulphonyl;

$R_3$ signifies hydrogen, $C_1$-$C_4$-alkyl or halogen;

$R_4$, $R_5$ and $R_6$, independently of one another, signify hydrogen, $C_1$-$C_6$-alkyl, which may be substituted by the group $A_1$; $C_3$-$C_7$-cycloalkyl, which may be substituted by the group $A_2$;

$C_3$-$C_7$-cycloalkyl, which may be interrupted by 1 to 2 oxygen atoms, sulphur or $NR_{11}$; $C_2$-$C_6$-alkenyl, which may be substituted by the group $A_3$; $C_3$-$C_6$-alkynyl, which may be substituted by the group $A_4$; $C_3$-$C_7$-cycloalkyl-$C_1$-$C_4$-alkyl, whereby the cycloalkyl group may be interrupted by 1 to 2 oxygen atoms, sulphur or $NR_{12}$; benzyl or phenyl which may in turn be substituted by halogen, $C_1$-$C_4$-alkyl, $C_1$-$C_4$-alkoxy, $C_1$-$C_4$-halogenalkyl, cyano, nitro, $C_1$-$C_4$-halogenalkoxy, $C_1$-$C_4$-alkylthio, $C_1$-$C_4$-alkylsulphinyl, $C_1$-$C_4$-alkylsulphonyl, $C_1$-$C_4$-dialkylamino, $C_1$-$C_4$-alkylcarbonyl, $C_1$-$C_4$-dialkylaminosulphonyl or $NR_{13}$—CO—$R_{14}$;

$R_{11}$ and $R_{12}$, independently of one another, signify hydrogen or $C_1$-$C_4$-alkyl;

$R_{13}$ and $R_{14}$, independently of one another, signify hydrogen or $C_1$-$C_4$-Alkyl;

$A_1$, $A_2$, $A_3$, $A_4$, independently of one another, are hydroxy, formyl, COOH, $C_1$-$C_6$-alkoxy, $C_1$-$C_4$-alkylthio, $C_1$-$C_4$-alkylsulphinyl, $C_1$-$C_4$-alkylsulphonyl, $OSO_2$— $C_1$-$C_4$-alkyl, $C_1$-$C_6$-alkylamino, $C_1$-$C_6$-dialkylamino, $C_1$-$C_6$-alkylaminocarbonyl, $C_1$-$C_6$-dialkylaminocarbonyl, nitro, halogen, cyano, $C_1$-$C_4$-alkoxyhalogen, $C_1$-$C_4$-alkylcarbonyl, $C_1$-$C_4$-alkoxycarbonyl or phenyl, whereby the phenyl group may in turn be substituted by halogen, $C_1$-$C_4$-alkyl, $C_1$-$C_4$-alkoxy, $C_1$-$C_4$-halogenalkyl, cyano, nitro, $C_1$-$C_4$-halogenalkoxy, $C_1$-$C_4$-alkylthio, $C_1$-$C_4$-alkylsulphinyl, $C_1$-$C_4$-alkylsulphonyl, $C_1$-$C_4$-alkylcarbonyl, $C_1$-$C_4$-dialkylaminosulphonyl or $NR_{15}$—CO—$R_{16}$;

$R_{15}$ and $R_{16}$, independently of one another, signify hydrogen or $C_1$-$C_4$-alkyl;

Q is the group $Q_1$

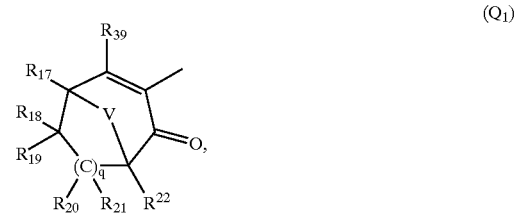

(Q1)

wherein $R_{39}$ signifies hydroxy, halogen, $C_1$-$C_6$-alkoxy, $C_1$-$C_6$-alkylcarbonyloxy, $C_1$-$C_6$-alkoxycarbonyloxy, $C_1$-$C_6$-dialkylamino, COOH, $C_1$-$C_6$-alkenylthio, $C_1$-$C_6$-alkenylsulphinyl, $C_1$-$C_6$-alkenylsulphonyl, $OSO_2$—$C_1$-$C_6$-alkyl, benzoyloxy or $OSO_2$-phenyl, whereby the phenyl and benzoyl groups may in turn be substituted by $C_1$-$C_4$-alkyl, $C_1$-$C_4$-halogenalkyl, $C_1$-$C_4$-alkoxy, $C_1$-$C_4$-halogenalkoxy, $C_1$-$C_4$-alkylcarbonyl, $C_1$-$C_4$-alkoxycarbonyl, halogen, nitro, COOH or cyano; V is $C_1$-$C_4$-alkylene, oxygen, sulphur, SO or $SO_2$;

$R_{17}$, $R_{18}$, $R_{19}$, $R_{20}$, $R_{21}$ and $R_{22}$, independently of one another, signify hydrogen, $C_1$-$C_6$-alkyl, $C_1$-$C_6$-alkoxycarbonyl, $C_2$-$C_6$-alkenyl, $C_2$-$C_6$-alkynyl, $C_1$-$C_6$-alkylthio, $C_1$-$C_6$-alkylsulphinyl, $C_1$-$C_6$-alkylsulphonyl, $C_1$-$C_4$-alkylaminosulphonyl, $C_1$-$C_4$-halogenalkyl, $C_1$-$C_4$-alkylamino, $C_1$-$C_4$-dialkylamino, $C_1$-$C_6$-alkoxy, cyano, nitro, halogen or phenyl, q is 1 or 2;

or Q is the group $Q_2$

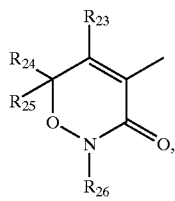

(Q₂)

or Q is the group $Q_3$

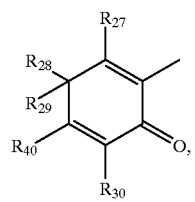

(Q₃)

wherein $R_{23}$ signifies hydroxy, halogen, $C_1$–$C_6$-alkoxy, $C_1$–$C_6$-alkylcarbonyloxy, $C_1$–$C_6$-alkoxycarbonyloxy, $C_1$–$C_6$-dialkylamino, COOH, $C_1$–$C_6$-alkylthio, $C_1$–$C_6$-alkylsulphinyl, $C_1$–$C_6$-alkylsulphonyl, $C_1$–$C_4$-alkoxycarbonyl-$C_1$–$C_4$-alkylthio, $C_1$–$C_4$-alkoxycarbonyl-$C_1$–$C_4$-alkylsulphinyl, $C_1$–$C_4$-alkoxycarbonyl-$C_1$–$C_4$-alkylsulphonyl, $C_1$–$C_6$-alkenylthio, $C_1$–$C_6$-alkenylsulphinyl, $C_1$–$C_6$-alkenylsulphonyl, $OSO_2$—$C_1$–$C_6$-alkyl, benzoyloxy, phenylthio, phenylsulphinyl, phenylsulphonyl or $OSO_2$-phenyl, whereby the phenyl and benzoyl groups may in turn be substituted by $C_1$–$C_4$-alkyl, $C_1$–$C_4$-halogenalkyl, $C_1$–$C_4$-alkoxy, $C_1$–$C_4$-halogenalkoxy, $C_1$–$C_4$-alkylcarbonyl, $C_1$–$C_4$-alkoxycarbonyl, halogen, nitro, COOH or cyano; $R_{24}$ and $R_{25}$, independently of one another, signify hydrogen, hydroxy, $C_1$–$C_6$-alkyl, $C_1$–$C_4$-alkoxy-$C_1$–$C_4$-alkyl, $C_2$–$C_6$-alkenyl, $C_2$–$C_6$-alkynyl, $C_1$–$C_6$-alkoxycarbonyl, $C_1$–$C_6$-alkylthio, $C_1$–$C_6$-alkylsulphinyl, $C_1$–$C_6$-alkylsulphonyl, $C_1$–$C_4$-alkylaminosulphonyl, $C_1$–$C_4$-halogenalkyl, $C_1$–$C_6$-alkylamino, $C_1$–$C_6$-dialkylamino, $C_1$–$C_6$-alkoxy, cyano, nitro, halogen or phenyl, which may in turn be substituted by $C_1$–$C_4$-alkyl, $C_1$–$C_4$-halogenalkyl, $C_1$–$C_4$-alkoxy, $C_1$–$C_4$-halogenalkoxy, $C_1$–$C_4$-alkylcarbonyl, $C_1$–$C_4$-alkoxycarbonyl, amino, $C_1$–$C_4$-alkylamino, $C_1$–$C_4$-dialkylamino, $C_1$–$C_6$-alkylthio, $C_1$–$C_6$-alkylsulphinyl, $C_1$–$C_6$-alkylsulphonyl, $C_1$–$C_4$-alkyl-$S(O)_2O$, $C_1$–$C_4$-halogenalkylthio, $C_1$–$C_4$-halogenalkylsulphinyl, $C_1$–$C_4$-halogenalkylsulphonyl, $C_1$–$C_4$-halogenalkyl-$S(O)_2O$, $C_1$–$C_4$-alkyl-$S(O)_2NH$, $C_1$–$C_4$-alkyl-$S(O)_2N(C_1$–$C_4$-alkyl), halogen, nitro, COOH or cyano; or $R_{24}$ and $R_{25}$ together form a $C_2$–$C_6$-alkylene bridge, $R_{26}$ signifies hydrogen, $C_1$–$C_4$-alkyl, $C_1$–$C_4$-alkoxycarbonyl or phenyl, which may in turn be substituted by $C_1$–$C_6$-alkyl, $C_1$–$C_6$-halogenalkyl, $C_1$–$C_6$-alkoxy, $C_1$–$C_6$-halogenalkoxy, $C_1$–$C_6$-alkylcarbonyl, $C_1$–$C_6$-alkoxycarbonyl, amino, $C_1$–$C_4$-alkylamino, $C_1$–$C_4$-dialkylamino, $C_1$–$C_6$-alkylthio, $C_1$–$C_6$-alkylsulphinyl, $C_1$–$C_6$-alkylsulphonyl, $C_1$–$C_4$-alkyl-$S(O)_2O$, $C_1$–$C_4$-halogenalkylthio, $C_1$–$C_4$-halogenalkylsulphinyl, $C_1$–$C_4$-halogenalkylsulphonyl, $C_1$–$C_4$-halogenalkyl-$S(O)_2O$, $C_1$–$C_4$-alkyl-$S(O)_2NH$, $C_1$–$C_4$-alkyl-$S(O)_2N(C_1$–$C_4$-alkyl), halogen, nitro, COOH or cyano;

wherein $R_{27}$ signifies hydroxy, halogen, $C_1$–$C_6$-alkoxy, $C_1$–$C_6$-alkylcarbonyloxy, $C_1$–$C_6$-alkoxycarbonyloxy, $C_1$–$C_6$-dialkylamino, COOH, $C_1$–$C_6$-alkylthio, $C_1$–$C_6$-alkylsulphinyl, $C_1$–$C_6$-alkylsulphonyl, $C_1$–$C_4$-alkoxycarbonyl-$C_1$–$C_4$-alkylthio, $C_1$–$C_4$-alkoxycarbonyl-$C_1$–$C_4$-alkylsulphinyl, $C_1$–$C_4$-alkoxycarbonyl-$C_1$–$C_4$-alkylsulphonyl, $C_1$–$C_6$-alkenylthio, $C_1$–$C_6$-alkenylsulphinyl, $C_1$–$C_6$-alkenylsulphonyl, $OSO_2$—$C_1$–$C_6$-alkyl, benzoyloxy, phenylthio, phenylsulphinyl, phenylsulphonyl or $OSO_2$-phenyl, whereby the phenyl and benzoyl groups may in turn be substituted by $C_1$–$C_4$-alkyl, $C_1$–$C_4$-halogenalkyl, $C_1$–$C_4$-alkoxy, $C_1$–$C_4$-halogenalkoxy, $C_1$–$C_4$-alkylcarbonyl, $C_1$–$C_4$-alkoxycarbonyl, halogen, nitro, COOH or cyano;

$R_{28}$, $R_{29}$ and $R_{40}$, independently of one another, signify hydrogen, hydroxy, $C_1$–$C_6$-alkyl, $C_1$–$C_4$-alkoxy-$C_1$–$C_4$-alkyl, $C_2$–$C_6$-alkenyl, $C_2$–$C_6$-alkynyl, $C_1$–$C_6$-alkoxycarbonyl, $C_1$–$C_6$-alkylthio, $C_1$–$C_6$-alkylsulphinyl, $C_1$–$C_6$-alkylsulphonyl, $C_1$–$C_4$-alkylaminosulphonyl, $C_1$–$C_4$-halogenalknyl, $C_1$–$C_6$-alkylamino, $C_1$–$C_6$-dialkylamino, $C_1$–$C_6$-alkoxy, cyano, nitro, halogen or phenyl, which may in turn be substituted by $C_1$–$C_4$-alkyl, $C_1$–$C_4$-halogenalkyl, $C_1$–$C_4$-alkoxy, $C_1$–$C_4$-halogenalkoxy, $C_1$–$C_4$-alkylcarbonyl, $C_1$–$C_4$-alkoxycarbonyl, amino, $C_1$–$C_4$-alkylamino, $C_1$–$C_4$-dialkylamino, $C_1$–$C_6$-alkylthio, $C_1$–$C_6$-alkylsulphinyl, $C_1$–$C_6$-alkylsulphonyl, $C_1$–$C_4$-alkyl-$S(O)_2O$, $C_1$–$C_4$-halogenalkylthio, $C_1$–$C_4$-halogenalkylsulphinyl, $C_1$–$C_4$-halogenalkylsulphonyl, $C_1$–$C_4$-halogenalkyl-$S(O)_2O$, $C_1$–$C_4$-alkyl-$S(O)_2NH$, $C_1$–$C_4$-alkyl-$S(O)_2N(C_1$–$C_4$-alkyl), halogen, nitro, COOH or cyano; or $R_{28}$ and $R_{29}$ together form a $C_2$–$C_6$-alkylene bridge, $R_{30}$ signifies $C_1$–$C_6$-alkyl, which may be substituted by a group $A_5$; $C_2$–$C_6$-alkenyl, which may be substituted by a group $A_6$; $C_2$–$C_6$-alkynyl, which may be substituted by a group $A_7$;

$A_5$, $A_6$ and $A_7$, independently of one another, are hydroxy, formyl, COOH, $C_1$–$C_6$-alkoxy, $C_1$–$C_4$-alkylthio, $C_1$–$C_4$-alkylsulphinyl, $C_1$–$C_4$-alkylsulphonyl, $OSO_2$—$C_1$–$C_4$-alkyl, $C_1$–$C_6$-alkylamino, $C_1$–$C_6$-dialkylamino, $C_1$–$C_6$-alkylaminocarbonyl, $C_1$–$C_6$-dialkylaminocarbonyl, nitro, halogen, cyano, $C_1$–$C_4$-alkoxyhalogen, $C_1$–$C_4$-alkylcarbonyl, $C_1$–$C_4$-alkoxycarbonyl or phenyl, whereby the phenyl is in turn substituted by halogen, $C_1$–$C_4$-alkyl, $C_1$–$C_4$-alkoxy, $C_1$–$C_4$-halogenalkyl, cyano, nitro, $C_1$–$C_4$-halogenalkoxy, $C_1$–$C_4$-alkylthio, $C_1$–$C_4$-alkylsulphinyl, $C_1$–$C_4$-alkylsulphonyl, $C_1$–$C_4$-alkylcarbonyl, $C_1$–$C_4$-dialkylaminosulphonyl or $NR_{31}$—CO—$R_{32}$;

$R_{31}$, $R_{32}$, independently of one another, signify hydrogen or $C_1$–$C_4$-alkyl;
or Q is the group $Q_4$

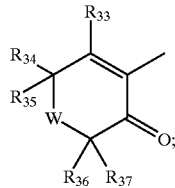

($Q_4$)

wherein
$R_{33}$ signifies hydroxy, halogen, $C_1$–$C_6$-alkoxy, $C_1$–$C_6$-alkylcarbonyloxy, $C_1$–$C_6$-alkoxycarbonyloxy $C_1$–$C_6$-dialkylamino, $C_1$–$C_6$-alkylthio, $C_1$–$C_6$-alkylsulphinyl, $C_1$–$C_6$-alkylsulphonyl, $C_1$–$C_4$-alkoxycarbonyl-$C_1$–$C_4$-alkylthio, $C_1$–$C_4$-alkoxycarbonyl-$C_1$–$C_4$-alkylsulphinyl, $C_1$–$C_4$-alkoxycarbonyl-$C_1$–$C_4$-alkylsulphonyl, $C_1$–$C_6$-alkenylthio, $C_1$–$C_6$-alkenylsulphinyl, $C_1$–$C_6$-alkenylsulphonyl, $OSO_2$—$C_1$–$C_6$-alkyl, benzoyloxy, phenylthio, phenylsulphinyl, phenylsulphonyl or $OSO_2$-phenyl, whereby the phenyl and benzoyl groups may in turn be substituted by $C_1$–$C_4$-alkyl, $C_1$–$C_4$-halogenalkyl, $C_1$–$C_4$-alkoxy, $C_1$–$C_4$-halogenalkoxy, $C_1$–$C_4$-alkylcarbonyl, $C_1$–$C_4$-alkoxycarbonyl, halogen, nitro, COOH or cyano;
W is oxygen, sulphur, SO, $SO_2$, $NR_{38}$ or C=O;
$R_{38}$ signifies hydrogen or $C_1$–$C_6$-alkyl;
$R_{34}$, $R_{35}$, $R_{36}$ and $R_{37}$, independently of one another, signify hydrogen, hydroxy, $C_1$–$C_6$-alkyl, $C_1$–$C_4$-alkoxy-$C_1$–$C_4$-alkyl, $C_2$–$C_6$-alkenyl, $C_2$–$C_6$-alkynyl, $C_1$–$C_6$-alkoxycarbonyl, $C_1$–$C_6$-alkylthio, $C_1$–$C_6$-alkylsulphinyl, $C_1$–$C_6$-alkylsulphonyl, $C_1$–$C_4$-alkylaminosulphonyl, $C_1$–$C_4$-halogenalkyl, $C_1$–$C_6$-alkylamino, $C_1$–$C_6$-dialkylamino, $C_1$–$C_6$-alkoxy, cyano, nitro, halogen or phenyl, which may in turn be substituted by $C_1$–$C_4$-alkyl, $C_1$–$C_4$-halogenalkyl, $C_1$–$C_4$-alkoxy, $C_1$–$C_4$-halogenalkoxy, $C_1$–$C_4$-alkylcarbonyl, $C_1$–$C_4$-alkoxycarbonyl, amino, $C_1$–$C_4$-alkylamino, $C_1$–$C_4$-dialkylamino, $C_1$–$C_6$-alkylthio, $C_1$–$C_6$-alkylsulphinyl, $C_1$–$C_6$-alkylsulphonyl, $C_1$–$C_4$-alkyl-S(O)$_2$O, $C_1$–$C_4$-halogenalkylthio, $C_1$–$C_4$-halogenalkylsulphinyl, $C_1$–$C_4$-halogenalkylsulphonyl, $C_1$–$C_4$-halogenalkyl-S(O)$_2$O, $C_1$–$C_4$-alkyl-S(O)$_2$NH, $C_1$–$C_4$-alkyl-S(O)$_2$N($C_1$–$C_4$-alkyl), halogen, nitro, COOH or cyano; or $R_{34}$ and $R_{35}$ together form a $C_2$–$C_6$-alkylene bridge, as well as agronomically acceptable salts, isomers and enantiomers of these compounds.

The invention similarly relates to the salts that may be formed by the compounds of formula I, especially those compounds of formula I in which $R_{23}$, $R_{27}$, $R_{33}$ and $R_{39}$ are hydroxy, with amines, alkali metal bases and alkaline earth metal bases, or quaternary ammonium bases.

Of the alkali metal hydroxides and alkaline earth metal hydroxides as salt-forming components, the hydroxides of lithium, sodium, potassium, magnesium or calcium are notable, especially those of sodium or potassium.

Examples of amines that are suitable for ammonium salt formation may be both ammonia and primary, secondary and tertiary $C_1$–$C_{18}$-alkylamines, $C_1$–$C_4$-hydroxyalkylamines and $C_2$–$C_4$-alkoxyalkylamines, for example methylamine, ethylamine, n-propylamine, isopropylamine, the four isomeric butylamines, n-amylamine, iso-amylamine, hexylamine, heptylamine, octylamine, nonylamine, decylamine, pentadecylamine, hexadecylamine, heptadecylamine, octadecylamine, methylethylamine, methyl-iso-propylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, di-iso-propylamine, di-n-butylamine, di-n-amylamine, di-iso-amylamine, dihexylamine, diheptylamine, dioctylamine, ethanolamine, n-propanolamine, iso-propanolamine, N,N-diethanolamine, N-ethylpropanolamine, N-butylethanolamine, allylamine, n-butenyl-2-amine, n-pentenyl-2-amine, 2,3-dimethylbutenyl-2-amine, di-butenyl-2-amine, n-hexenyl-2-amine, propylenediamine, trimethylamine, triethylamine, tri-n-propylamine, tri-iso-propylamine, tri-n-butylamine, tri-iso-butylamine, tri-sec.-butylamine, tri-n-amylamine, methoxyethylamine and ethoxyethylamine; heterocyclic amines such as pyridine, quinoline, iso-quinoline, morpholine, piperidine, pyrrolidine, indoline, quinuclidine and azepine; primary arylamines such as anilines, methoxyanilines, ethoxyanilines, o,m,p-toluidines, phenylenediamines, benzidines, naphthylamines and o,m,p-chloroanilines; but especially triethylamine, iso-propylamine and di-iso-propylamine.

The alkyl and alkylene groups present in the definitions of the substituents may be straight-chained or branched and are, for example, methyl, ethyl, n-propyl, iso-propyl, n-butyl, sec.-butyl, iso-butyl, tert.-butyl, pentyl and hexyl, as well as the branched isomers thereof. Alkoxy, alkenyl, alkenylene, alkynyl and alkynylene groups are derived from the said alkyl groups. The alkenyl, alkenylene, alkynyl and alkynylene groups may be mono- or multi-unsaturated.

Halogen normally signifies fluorine, chlorine, bromine or iodine. The same applies also to halogen in conjunction with other definitions such as halogenalkyl or halogenphenyl.

Halogenalkyl groups preferably have a chain length of 1 to 6 carbon atoms. Halogenalkyl is for example fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl.

Alkoxy groups preferably have a chain length of 1 to 6 carbon atoms. Alkoxy is for example methoxy, ethoxy, propoxy, i-propoxy, n-butoxy, iso-butoxy, sec.-butoxy and tert.-butoxy as well as the isomers pentyloxy and hexyloxy; preferably methoxy and ethoxy. Alkylcarbonyl is preferably acetyl or propionyl. Alkoxycarbonyl signifies for example methoxycarbonyl, ethoxycarbonyl, propoxycarbonyl, iso-propoxycarbonyl, n-butoxycarbonyl, iso-butoxycarbonyl, sec.-butoxycarbonyl or tert.-butoxycarbonyl; preferably methoxycarbonyl or ethoxycarbonyl. Halogenalkoxy groups preferably have a chain length of 1 to 6 carbon atoms. Halogenalkoxy is e.g. fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2-chloroethoxy and trifluoromethoxy. Alkylthio groups preferably have a chain length of 1 to 6 carbon atoms. Alkylthio is for example methylthio, ethylthio, propylthio, iso-propylthio, n-butylthio, iso-butylthio, sec.-butylthio or tert.-butylthio, preferably methylthio and ethylthio. Alkylsulphinyl is for example methylsulphinyl, ethylsulphinyl, propylsulphinyl, iso-propylsulphinyl, n-butylsulphinyl, iso-butylsulphinyl, sec.-butylsulphinyl, tert.-butylsulphinyl; preferably methylsulphinyl and ethylsulphinyl.

$C_3$–$C_7$-cycloalkyl, which is interrupted by oxygen, is for example oxiranyl, oxetanyl, tetrahydrofuranyl, dioxolanyl, oxacyclohexyl, dioxacyclohexyl, oxacycloheptyl or dioxacycloheptyl.

$C_3$–$C_7$-cycloalkyl-$C_1$–$C_3$-alkyl, which may be interrupted by oxygen, is for example oxiranylmethyl, oxetanyl-ethyl, tetrahydrofuranyl-n-propyl, dioxolanyl-$C_1$–$C_3$-alkyl, oxacyclohexyl-$C_1$–$C_3$-alkyl, dioxacyclohexyl-$C_1$–$C_3$-alkyl, oxacycloheptyl-$C_1$–$C_3$-alkyl or Dioxacycloheptyl-$C_1$–$C_3$-alkyl.

Alkylsulphonyl is for example methylsulphonyl, ethylsulphonyl, propylsulphonyl, iso-propylsulphonyl, n-butylsulphonyl, iso-butylsulphonyl, sec.-butylsulphonyl or tert.-butylsulphonyl; preferably methylsulphonyl or ethylsulphonyl Alkoxyalkoxy groups preferably have a chain length of 2 to 4 carbon atoms.

Examples of alkoxyalkoxy are: methoxymethoxy, methoxyethoxy, methoxypropoxy, ethoxymethoxy, ethoxyethoxy, propoxymethoxy or butoxybutoxy.

Alkylamino is for example methylamino, ethylamino, n-propylamino, isopropylamino or the isomeric butylamines. Dialkylamino is for example dimethylamino, methylethylamino, diethylamino, n-propylmethylamino, dibutylamino and diisopropylamino. Preference is given to alkylamino groups with a chain length of 1 to 4 carbon atoms. Alkoxyalkyl groups preferably have 2 to 4 carbon atoms. Alkoxyalkyl signifies for example methoxymethyl, methoxyethyl, ethoxymethyl, ethoxyethyl, n-propoxymethyl, n-propoxyethyl, isopropoxymethyl or isopropoxyethyl. Alkylthioalkyl groups preferably have 2 to 4 carbon atoms. Alkylthioalkyl signifies for example methylthiomethyl, methylthioethyl, ethylthiomethyl, ethylthioethyl, n-propylthiomethyl, n-propylthioethyl, isopropylthiomethyl, isopropylthioethyl, butylthiomethyl, butylthioethyl or butylthiobutyl. The cycloalkyl groups preferably have 3 to 6 ring carbon atoms, for example cyclopropyl, cyclobutyl, cyclopentyl and cyclohexyl. Phenyl, even as part of a substituent, such as phenoxy, benzyl, benzyloxy, benzoyl, phenylthio, phenylalkyl or phenoxyalkyl, may be present in substituted form.

Preference is given to compounds of formula I, in which $R_1$ and $R_2$, independently of one another, signify halogen, cyano, nitro, amino, $C_1$–$C_6$-alkyl, $C_1$–$C_6$-alkoxy, $C_1$–$C_4$-alkoxy-$C_1$–$C_4$-alkyl, $C_1$–$C_6$-halogenalkyl, $C_2$–$C_6$-alkenyl, $C_2$–$C_6$-alkynyl, $C_1$–$C_6$-alkoxycarbonyl, $C_1$–$C_6$-alkylcarbonyl, $C_1$–$C_6$-alkylthio, $C_1$–$C_6$-alkylsulphinyl, $C_1$–$C_6$-alkylsulphonyl, $C_1$–$C_6$-dialkylaminosulphonyl, $C_1$–$C_6$-alkylaminosulphonyl, $C_1$–$C_6$-halogenalkoxy, $OSO_2$—$C_1$–$C_4$-alkyl, $C_1$–$C_6$-halogenalkylthio, $C_1$–$C_6$-halogen-alkylsulphinyl, $C_1$–$C_6$-halogenalkylsulphonyl, phenylthio, phenylsulphinyl or phenylsulphonyl and $R_{33}$ signifies hydroxy, halogen, $C_1$–$C_6$-alkoxy, $C_1$–$C_6$-alkylcarbonyloxy, $C_1$–$C_6$-alkoxycarbonyloxy, $C_1$–$C_6$-dialkylamino, COOH, $C_1$–$C_6$-alkylthio, $C_1$–$C_6$-alkylsulphinyl, $C_1$–$C_6$-alkylsulphonyl, $C_1$–$C_4$-alkoxycarbonyl-$C_1$–$C_4$-alkylthio, $C_1$–$C_4$-alkoxycarbonyl-$C_1$–$C_4$-alkylsulphinyl, $C_1$–$C_4$-alkoxycarbonyl-$C_1$–$C_4$-alkylsulphonyl, $C_1$–$C_6$-alkenylthio, $C_1$–$C_6$-alkenylsulphinyl, $C_1$–$C_6$-alkenylsulphonyl, $OSO_2$—$C_1$–$C_6$-alkyl, benzoyloxy, phenylthio, phenylsulphinyl, phenylsulphonyl or $OSO_2$-phenyl, whereby the phenyl and benzoyl groups may in turn be substituted by $C_1$–$C_4$-alkyl, $C_1$–$C_4$-halogenalkyl, $C_1$–$C_4$-alkoxy, $C_1$–$C_4$-halogenalkoxy, $C_1$–$C_4$-alkylcarbonyl, $C_1$–$C_4$-alkoxycarbonyl, halogen, nitro, COOH or cyano.

Further preferred compounds of formula I are characterised in that Q is $Q_1$ or $Q_2$, whereby in the group $Q_2$, $R_{24}$, $R_{25}$ and $R_{26}$ are preferably hydrogen or $C_1$–$C_6$-alkyl. $R_{23}$ and $R_{39}$ denote hydroxy in particular. Also notable are those compounds of formula I, in which X is $L_1$-$Y_1$-$R_4$. Of this group, the compounds in which $L_1$ signifies methylene are preferred. In a further preferred group of compounds of formula I, $R_2$ signifies $C_1$–$C_6$-alkylsulphonyl. Also of interest are compounds of formula I, in which $R_1$ signifies methyl.

Particularly preferred individual compounds falling within the scope of formula I are: 4-hydroxy-3-(4-methylsulphonyl-3-methoxymethyl-2-methyl-benzoyl)-bicyclo[3.2.1]oct-3-en-2-one and 5-hydroxy-4-(4-methylsulphonyl-3-methoxymethyl-2-methyl-benzoyl)-2,6,6-trimethyl-6.H.-[1,2]oxazin-3-one.

The compounds of formula I may be produced by known processes which are described, for example, in U.S. Pat. Nos. 5,565,410, 5,608,101 and EP-A-0 282 944, whereby e.g. a compound of formula II

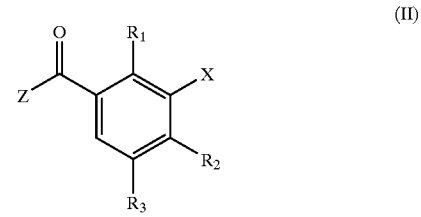

wherein $R_1$, $R_2$, $R_3$ and X have the significances given under formula I and Z signifies a leaving group, preferably halogen, especially chlorine or cyano, is reacted with a compound of formula III

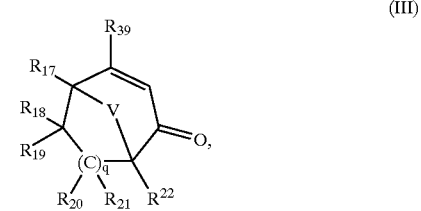

wherein the substituents are defined as in group $Q_1$, or with a compound of formula IV

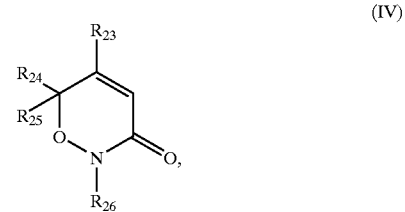

wherein the substituents are defined as in group $Q_2$, or with a compound of formula V

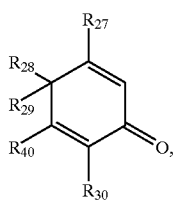

(V)

wherein the substituents are defined as in group $Q_3$, or with a compound of formula VI

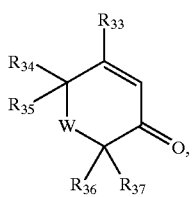

(VI)

wherein the substituents are defined as in group $Q_4$ and correspondingly $R_{39}$, $R_{23}$, $R_{27}$ and $R_{33}$ signify hydroxy, optionally in the presence of a base. The compounds of formulae II, III, IV or V are known from U.S. Pat. Nos. 5,565,410, 5,608,101 and EP-A-0 282 944 or may be produced analogously to the processes disclosed therein.

The reactions for obtaining the compounds of formula I are advantageously carried out in aprotic inert organic solvents. Such solvents are hydrocarbons such as benzene, toluene, xylene or cyclohexane, chlorinated hydrocarbons such as dichloromethane, trichloromethane, tetrachloromethane or chlorobenzene, ethers such as diethyl ether, ethylene glycol dimethyl ether, diethylene glycol dimethyl ether, tetrahydrofuran or dioxane, nitriles such as acetonitrile or propionitrile, amides such as N,N-dimethyl formamide, diethyl formamide or N-methylpyrrolidinone. The reaction temperatures are preferably in the range from −20° to +120° C. The reactions are usually slightly exothermic and can as a rule be carried out at room temperature. The reaction mixture can be heated for a brief time to boiling point to shorten the reaction time or also to initiate the reaction. The reaction times can also be shortened by addition of a few drops of a base as reaction catalyst. Particularly suitable bases are tertiary amines such as trimethylamine, triethylamine, quinuclidine, 1,4-diazabicyclo[2.2.2]octane, 1,5-diazabicyclo[4.3.0]non-5-ene or 1,5-diazabicyclo[5.4.0]undec-7-ene. Further suitable bases are also inorganic bases, typically hydrides such as sodium or calcium hydride, hydroxides such as sodium or potassium hydroxide, carbonates such as sodium and potassium carbonate, or hydrogen carbonates such as potassium and sodium hydrogen carbonate.

The compounds of formula I can be isolated in conventional manner by concentrating the reaction mixture and/or removing the solvent by evaporation and by recrystallising or triturating the solid residue in solvents in which they are not readily soluble, typically ethers, aromatic hydrocarbons or chlorinated hydrocarbons.

The compounds of formula I or compositions containing them may be used according to this invention by all standard methods of application used in agriculture, including preemergence application, postemergence application and seed dressing, as well as by different methods and techniques such as controlled release. For controlled release, a solution of the herbicide is applied to a mineral granular carrier or to a polymerised granulate (urea/formaldehyde) and then dried. A coating can then be additionally applied (coated granules) that allows the active ingredient to be released at a controlled rate over a specific period of time.

The compounds of formula I may be used as herbicides in unmodified form, i.e. as obtained in the synthesis. Preferably they are processed in conventional manner with the auxiliary agents customarily employed in formulation technology to emulsifiable concentrates, directly sprayable or dilutable solutions, dilute emulsions, wettable powders, soluble powders, dusts, granulates or microcapsules. Such formulations are described, for example, in WO 97/34485 on pages 9 to 13. As with the type of agents, the methods of application such as spraying, atomising, dusting, wetting, scattering or pouring, are selected in accordance with the intended objectives and the prevailing circumstances.

The formulations, i.e. the agents, preparations, or compositions containing the compound of formula I or at least one compound of formula I and usually one or more than one liquid or solid formulation assistant, are prepared in known manner, e.g. by homogeneously mixing and/or grinding the herbicide with said formulation auxiliaries, typically solvents or solid carriers. Surface-active compounds (surfactants) may additionally be used for preparing the formulations. Examples of solvents and solid carriers are described in WO 97/34485 on page 6.

Depending on the herbicide of formula I to be formulated, suitable surface-active compounds are nonionic, cationic and/or anionic surfactants and surfactant mixtures having good emulsifying, dispersing and wetting properties.

Examples of suitable anionic, nonionic, and cationic surfactants are listed for example in WO 97/34485 on pages 7 and 8.

Also the surfactants customary in the art of formulation and described, inter alia, in "McCutcheon's Detergents and Emulsifiers Annual" MC Publishing Corp., Ridgewood N.J., 1981, Stache, H., "Tensid-Taschenbuch" (Handbook of Surfactants), Carl Hanser Verlag, Munich/Vienna, 1981, and M. and J. Ash, "Encyclopedia of Surfactants", Vol I–III, Chemical Publishing Co., New York, 1980–81, are suitable for manufacture of the herbicides according to the invention.

The herbicidal compositions will as a rule contain from 0.1 to 99% by weight, preferably from 0.1 to 95% by weight, of herbicide, from 1 to 99.9% by weight, preferably from 5 to 99.8% by weight, of a solid or liquid adjuvant, and from 0 to 25% by weight, preferably from 0.1 to 25% by weight, of a surfactant. Whereas it is preferred to formulate commercial products as concentrates, the end user will normally use dilute formulations. The compositions may also contain further ingredients, such as: stabilisers, e.g. where appropriate epoxidised vegetable oils (epoxidised coconut oil, rapeseed oil, or soybean oil); anti-foaming agents, typically silicone oil; preservatives; viscosity regulators; binders; and tackifiers; as well as fertilisers or other chemical agents.

The compounds of formula I are usually applied with success to the plants or the locus thereof in concentrations of 0.001 to 4 kg/ha, preferably 0.005 to 2 kg/ha. The concentration required to achieve the desired action can be determined by experimentation. It will depend on the type of action, the development stage of the cultivated plant and of the weed, as well as on the application (locus, time, method), and as a resulty of these variables can vary over a wide range.

The compounds of formula I have excellent herbicidal and growth inhibiting properties, which make them suitable for application in crops of cultivated plants, especially in cereals, cotton, soybeans, sugar beet, sugar cane, plantations, rape, maize, and rice, and for the non-selective control of weeds. Crops will also be understood to mean those crops that have been made tolerant to herbicides or classes of herbicides by conventional breeding or genetic engineering methods. The weeds to be controlled may be monocot as well as dicot weeds, typically Stellaria, Nasturtium, Agrostis, Digitaria, Avena, Setaria, Sinapis, Lolium, Solanum, Echinochloa, Scirpus, Monochoria, Sagittaria, Bromus, Alopecurus, *Sorghum halepense,* Rottboellia, Cyperus, Abutilon, Sida, Xanthium, Amaranthus, Chenopodium, ipomoea, Chrysanthemum, Galium, Viola, and Veronica.

The invention is illustrated by the following non-limitative Examples.

PREPARATION EXAMPLES

Example P1

Preparation of 4-methylsulphonyl-3-methoxymethyl-2-methylbenzoic acid chloride

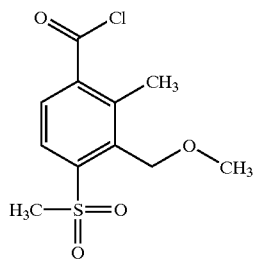

A solution of 1.5 g (5.8 mmols) of 4-methylsulphonyl-3-methoxymethyl-2-methylbenzoic acid in 15 ml of methylene chloride produced in accordance with EP-A-0 282 944 is mixed at a temperature of 20° C. with 2 drops of DMF. Then, whilst cooling lightly, a solution of 1.0 ml (11.6 mmols) of oxalyl chloride in 2 ml of methylene chloride is added dropwise. The reaction mixture is stirred until the evolution of gas has ended. Subsequently, the solvent is distilled off. The 4-methylsulphonyl-3-methoxymethyl-2-methylbenzoic acid chloride is used without further purification directly for the next step of the process.

Example P2

Preparation of 4-hydroxy-3-(4-methylsulphonyl-3-methoxymethyl-2-methylbenzoyl)-bicyclo[3.2.1]oct-3-en-2-one

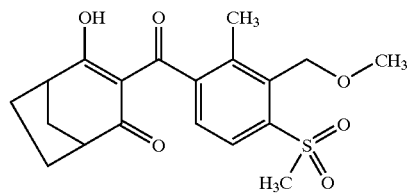

0.8 g (5.8 mmols) of bicyclo[3.2.1]octan-2,4-dione (the preparation thereof is described for example in U.S. Pat. No. 5,608,101 and in the references cited therein) are dissolved in 15 ml of methylene chloride at 20° C. The solution is mixed with 0.97 ml of triethylamine and cooled to a temperature of 0° C. Then, a solution of 1.6 g (5.8 mmols) of 4-methylsulphonyl-3-methoxymethyl-2-methylbenzoic acid chloride in 10 ml of methylene chloride is added dropwise. The reaction mixture is stirred for half an hour at a temperature of 0° C. and is subsequently diluted with methylene chloride. After washing and drying, the organic phase is concentrated by evaporation. 2.23 g of 4-methylsulphonyl-3-methoxymethyl-2-methylbenzoic acid-4-oxo-bicyclo [3.2.1]oct-2-en-2-yl-ester is obtained in amorphous form. This can be used for the next step without purification.

2.23 g (5.8 mmols) of 4-methylsulphonyl-3-methoxymethyl-2-methyl-benzoic acid-4-oxo-bicyclo [3.2.1]oct-2-en-2-yl-ester and 1.6 ml (11.6 mmols) of triethylamine are dissolved in 20 ml of acetonitrile. 0.2 ml of acetocyanohydrin are added at a temperature of 20° C. After stirring for 20 hours, the mixture is worked up and the crude product is purified by thick-layer chromatography. 1.0 g of 4-hydroxy-3-(4-methylsulphonyl-3-methoxymethyl-2-methylbenzoyl)-bicyclo[3.2.1]oct-3-en-2-one is obtained in amorphous form.

Example P3

Preparation of 5-hydroxy-4-(4-methylsulphonyl-3-methoxymethyl-2-methylbenzoyl)-2,6,6-trimethyl-6.H.-[1,2]oxazin-3-one

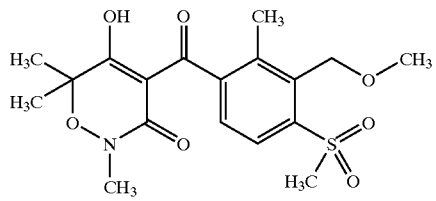

0.79 g (5.04 mmols) of 2,6,6-trimethyl-2H-1,2-oxazin-3, 5-dione (the preparation thereof is described for example in U.S. Pat. No. 5,565,410), 15 ml of methylene chloride and 0.97 ml of triethylamine are prepared, and at a temperature of 0° C., a solution of 1.3 g (4.7 mmols) of 4-methylsulphonyl-3-methoxymethyl-2-methylbenzoic acid chloride in 10 ml methylene chloride is added dropwise. After stirring for 30 minutes, the solution is diluted with methylene chloride. The reaction solution is subsequently acidified with diluted hydrochloric acid, the organic phase separated, dried and concentrated. 2.0 g of 4-methylsulphonyl-3-methoxymethyl-2-methyl-benzoic acid-2,6,6-trimethyl-5-oxo-5,6-dihydro-2.H.-[1,2]oxazin-3-yl-ester are obtained in amorphous form. The product may be further used directly without purification.

2.0 g (5.04 mmols) of 4-methylsulphonyl-3-methoxymethyl-2-methyl-benzoic acid-2,6,6-trimethyl-5-oxo-5,6-dihydro-2.H.-[1,2]oxazin-3-yl-ester are dissolved in a mixture of 35 ml of acetonitrile and 10 ml of methylene chloride, then 1.4 ml (10.08 mmols) of triethylamine and 0.18 ml of acetocyanohydrin are added. After stirring for 20 hours at a temperature of 20° C. and then working up, recrystallisation is effected, and finally hydroxy-4-(4-methylsulphonyl-3-methoxymethyl-2-methyl-benzoyl)-2,6, 6-trimethyl-6.H.-[1,2]oxazin-3-one is obtained with a melting point of 157° C.

The substances named in the following Tables 1 to 4 may also be prepared analogously to the methods described above. In Tables 1 to 4, X denotes the following groups:
$X_1=CH_2OCH_3$, $X_2=CH_2OC_2H_5$, $X_3=CH_2OH$,
$X_4=CH_2CH_2OCH_3$, $X_5=CH_2CH_2OC_2H_5$, $X_6=CH_2CH_2$ $OCH_2CH_2OCH_3$, $X_7=CH_2CH_2OCH_2CH_2OC_2H_5$, $X_8=CH(CH_3)OC_2H_5$, $X_{10}=CH_2OCH_2CH=CH_2$, $X_{11}=CH_2OCH_2CH_2CH_3$, $X_{12}=CH(C_2H_5)OC_2H_5$, $X_{13}=C(CH_3)_2OH$, $X_{14}=CH_2CH_2OCH(CH_3)_2$, $X_{15}=CH_2SO_2CH_3$, $X_{16}=CH_2N(CH_3)C_2H_5$, $X_{17}=CH_2NHCH_3$, $X_{18}=CH_2OCH(CH_3)_2$, $X_{19}=C(CH_3)_2OCH_3$, $X_{20}=CH_2CH_2OH$, $X_{21}=CH_2OCH_2CCH$, $X_{22}=C(CH_3)_2OC_2H_5$, $X_{23}=CH(C_2H_5)OCH_3$, $X_{24}=CH(CH_3)OH$, $X_{25}=CH(OH)C_2H_5$, $X_{26}=CH_2SCH_3$, $X_{27}=CH_2N(CH_3)_2$, $X_{28}=CH_2CH_2N(CH_3)_2$, $X_{29}=CH_2OCOCH_3$, $X_{30}=CH_2OPh$, $X_{31}=CH_2CH_2OPh$, $X_{32}=CH_2OCH_2CH_2OCH_3$, $X_{33}=CH_2OCH_2CH_2OC_2H_5$, $X_{34}=$ —$CH_2O$-cyclopropyl $X_{35}=$ —$CH_2O$-$CH_2$-cyclopropyl $X_{36}=$ —$CH_2O$-cyclopentyl $X_{37}=$ —$CH_2O$-tetrahydrofuranyl $X_{38}=$ —$CH_2O$-tetrahydropyranyl (with $CH_2O$ on ring)

$X_{39}=$ —$CH_2O$-$CH_2$-oxiranyl $X_{40}=$ —$CH_2O$-$CH_2$-tetrahydrofuranyl $X_{41}=$ —$CH_2O$-oxetanyl $X_{42}=$ —$CH_2O$-oxetanyl

TABLE 1

Compounds of formula (Ia):

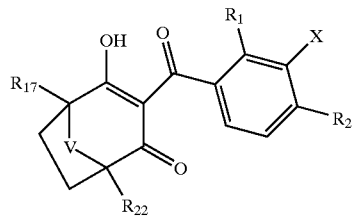

(Ia)

| Comp. No. | V | $R_{17}$ | $R_{22}$ | $R_1$ | X | $R_2$ | Phys. data |
|---|---|---|---|---|---|---|---|
| 1,001 | $CH_2$ | H | H | $CH_3$ | $X_1$ | $SO_2CH_3$ | resin |
| 1,002 | $CH_2$ | H | H | $CH_3$ | $X_2$ | $SO_2CH_3$ | — |
| 1,003 | $CH_2$ | H | H | $CH_3$ | $X_3$ | $SO_2CH_3$ | — |
| 1,004 | $CH_2$ | H | H | $CH_3$ | $X_4$ | $SO_2CH_3$ | — |
| 1,005 | $CH_2$ | H | H | $CH_3$ | $X_5$ | $SO_2CH_3$ | — |
| 1,006 | $CH_2$ | H | H | $CH_3$ | $X_6$ | $SO_2CH_3$ | — |
| 1,007 | $CH_2$ | H | H | $CH_3$ | $X_7$ | $SO_2CH_3$ | — |
| 1,008 | $CH_2$ | H | H | $CH_3$ | $X_8$ | $SO_2CH_3$ | — |
| 1,009 | $CH_2$ | H | H | $CH_3$ | $X_9$ | $SO_2CH_3$ | — |
| 1,010 | $CH_2$ | H | H | $CH_3$ | $X_{10}$ | $SO_2CH_3$ | — |
| 1,011 | $CH_2$ | H | H | $CH_3$ | $X_{11}$ | $SO_2CH_3$ | — |
| 1,012 | $CH_2$ | H | H | $CH_3$ | $X_{12}$ | $SO_2CH_3$ | — |
| 1,013 | $CH_2$ | H | H | $CH_3$ | $X_{13}$ | $SO_2CH_3$ | — |
| 1,014 | $CH_2$ | H | H | $CH_3$ | $X_{14}$ | $SO_2CH_3$ | — |
| 1,015 | $CH_2$ | H | H | $CH_3$ | $X_{15}$ | $SO_2CH_3$ | — |
| 1,016 | $CH_2$ | H | H | $CH_3$ | $X_{16}$ | $SO_2CH_3$ | — |
| 1,017 | $CH_2$ | H | H | $CH_3$ | $X_{17}$ | $SO_2CH_3$ | — |
| 1,018 | $CH_2$ | H | H | $CH_3$ | $X_{18}$ | $SO_2CH_3$ | — |
| 1,019 | $CH_2$ | H | H | $CH_3$ | $X_{19}$ | $SO_2CH_3$ | — |
| 1,020 | $CH_2$ | H | H | $CH_3$ | $X_{20}$ | $SO_2CH_3$ | — |
| 1,021 | $CH_2$ | H | H | $CH_3$ | $X_{21}$ | $SO_2CH_3$ | — |
| 1,022 | $CH_2$ | H | H | $CH_3$ | $X_{22}$ | $SO_2CH_3$ | — |
| 1,023 | $CH_2$ | H | H | $CH_3$ | $X_{23}$ | $SO_2CH_3$ | — |
| 1,024 | $CH_2$ | H | H | $CH_3$ | $X_{24}$ | $SO_2CH_3$ | — |
| 1,025 | $CH_2$ | H | H | $CH_3$ | $X_{25}$ | $SO_2CH_3$ | — |
| 1,026 | $CH_2$ | H | H | $CH_3$ | $X_{26}$ | $SO_2CH_3$ | — |
| 1,027 | $CH_2$ | H | H | $CH_3$ | $X_{27}$ | $SO_2CH_3$ | — |
| 1,028 | $CH_2$ | H | H | $CH_3$ | $X_{28}$ | $SO_2CH_3$ | — |
| 1,029 | $CH_2$ | H | H | $CH_3$ | $X_{29}$ | $SO_2CH_3$ | — |
| 1,030 | $CH_2$ | H | H | $CH_3$ | $X_{30}$ | $SO_2CH_3$ | — |
| 1,031 | $CH_2$ | H | H | $CH_3$ | $X_{31}$ | $SO_2CH_3$ | — |
| 1,032 | $CH_2$ | H | H | $CH_3$ | $X_{32}$ | $SO_2CH_3$ | — |
| 1,033 | $CH_2$ | H | H | $CH_3$ | $X_{33}$ | $SO_2CH_3$ | — |
| 1,034 | $CH_2$ | H | H | $CH_3$ | $X_{34}$ | $SO_2CH_3$ | — |
| 1,035 | $CH_2$ | H | H | $CH_3$ | $X_{35}$ | $SO_2CH_3$ | — |
| 1,036 | $CH_2$ | H | H | $CH_3$ | $X_{36}$ | $SO_2CH_3$ | — |
| 1,037 | $CH_2$ | H | H | $CH_3$ | $X_{37}$ | $SO_2CH_3$ | — |
| 1,038 | $CH_2$ | H | H | $CH_3$ | $X_{38}$ | $SO_2CH_3$ | — |
| 1,039 | $CH_2$ | H | H | $CH_3$ | $X_{39}$ | $SO_2CH_3$ | — |
| 1,040 | $CH_2$ | H | H | $CH_3$ | $X_{40}$ | $SO_2CH_3$ | — |
| 1,041 | $CH_2$ | H | H | $CH_3$ | $X_{41}$ | $SO_2CH_3$ | — |
| 1,042 | $CH_2$ | H | H | $CH_3$ | $X_{42}$ | $SO_2CH_3$ | — |
| 1,043 | $CH_2$ | H | H | $CH_3$ | $X_1$ | $SCH_3$ | — |
| 1,044 | $CH_2$ | H | H | $CH_3$ | $X_2$ | $SCH_3$ | — |
| 1,045 | $CH_2$ | H | H | $CH_3$ | $X_3$ | $SCH_3$ | — |
| 1,046 | $CH_2$ | H | H | $CH_3$ | $X_4$ | $SCH_3$ | — |
| 1,047 | $CH_2$ | H | H | $CH_3$ | $X_5$ | $SCH_3$ | — |
| 1,048 | $CH_2$ | H | H | $CH_3$ | $X_6$ | $SCH_3$ | — |
| 1,049 | $CH_2$ | H | H | $CH_3$ | $X_7$ | $SCH_3$ | — |
| 1,050 | $CH_2$ | H | H | $CH_3$ | $X_{10}$ | $SCH_3$ | — |
| 1,051 | $CH_2$ | H | H | $CH_3$ | $X_{15}$ | $SCH_3$ | — |
| 1,052 | $CH_2$ | H | H | $CH_3$ | $X_{20}$ | $SCH_3$ | — |
| 1,053 | $CH_2$ | H | H | $CH_3$ | $X_{21}$ | $SCH_3$ | — |
| 1,054 | $CH_2$ | H | H | $CH_3$ | $X_{26}$ | $SCH_3$ | — |
| 1,055 | $CH_2$ | H | H | $CH_3$ | $X_{27}$ | $SCH_3$ | — |
| 1,056 | $CH_2$ | H | H | $CH_3$ | $X_{29}$ | $SCH_3$ | — |
| 1,057 | $CH_2$ | H | H | $CH_3$ | $X_{30}$ | $SCH_3$ | — |
| 1,058 | $CH_3$ | $CH_3$ | $CH_3$ | $CH_3$ | $X_1$ | $SO_2CH_3$ | — |
| 1,059 | $CH_3$ | $CH_3$ | $CH_3$ | $CH_3$ | $X_2$ | $SO_2CH_3$ | — |
| 1,060 | $CH_3$ | $CH_3$ | $CH_3$ | $CH_3$ | $X_4$ | $SO_2CH_3$ | — |
| 1,061 | $CH_3$ | $CH_3$ | $CH_3$ | $CH_3$ | $X_{10}$ | $SO_2CH_3$ | — |
| 1,062 | $CH_3$ | $CH_3$ | $CH_3$ | $CH_3$ | $X_{15}$ | $SO_2CH_3$ | — |
| 1,063 | $CH_3$ | $CH_3$ | $CH_3$ | $CH_3$ | $X_{21}$ | $SO_2CH_3$ | — |
| 1,064 | $CH_3$ | $CH_3$ | $CH_3$ | $CH_3$ | $X_{26}$ | $SO_2CH_3$ | — |
| 1,065 | O | $CH_3$ | $CH_3$ | $CH_3$ | $X_1$ | $SO_2CH_3$ | — |
| 1,066 | O | $CH_3$ | $CH_3$ | $CH_3$ | $X_2$ | $SO_2CH_3$ | — |
| 1,067 | O | $CH_3$ | $CH_3$ | $CH_3$ | $X_4$ | $SO_2CH_3$ | — |
| 1,068 | O | $CH_3$ | $CH_3$ | $CH_3$ | $X_{10}$ | $SO_2CH_3$ | — |
| 1,069 | O | $CH_3$ | $CH_3$ | $CH_3$ | $X_{15}$ | $SO_2CH_3$ | — |
| 1,070 | O | $CH_3$ | $CH_3$ | $CH_3$ | $X_{21}$ | $SO_2CH_3$ | — |
| 1,071 | O | $CH_3$ | $CH_3$ | $CH_3$ | $X_{26}$ | $SO_2CH_3$ | — |
| 1,072 | $CH_2$ | H | H | Cl | $X_1$ | $SO_2CH_3$ | — |
| 1,073 | $CH_2$ | H | H | Cl | $X_2$ | $SO_2CH_3$ | — |
| 1,074 | $CH_2$ | H | H | Cl | $X_3$ | $SO_2CH_3$ | — |
| 1,075 | $CH_2$ | H | H | Cl | $X_4$ | $SO_2CH_3$ | — |
| 1,076 | $CH_2$ | H | H | Cl | $X_5$ | $SO_2CH_3$ | — |
| 1,077 | $CH_2$ | H | H | Cl | $X_6$ | $SO_2CH_3$ | — |
| 1,078 | $CH_2$ | H | H | Cl | $X_7$ | $SO_2CH_3$ | — |
| 1,079 | $CH_2$ | H | H | Cl | $X_8$ | $SO_2CH_3$ | — |
| 1,080 | $CH_2$ | H | H | Cl | $X_9$ | $SO_2CH_3$ | — |
| 1,081 | $CH_2$ | H | H | Cl | $X_{10}$ | $SO_2CH_3$ | — |
| 1,082 | $CH_2$ | H | H | Cl | $X_{11}$ | $SO_2CH_3$ | — |
| 1,083 | $CH_2$ | H | H | Cl | $X_{12}$ | $SO_2CH_3$ | — |

TABLE 1-continued

Compounds of formula (Ia):

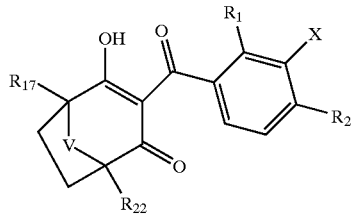

(Ia)

| Comp. No. | V | $R_{17}$ | $R_{22}$ | $R_1$ | X | $R_2$ | Phys. data |
|---|---|---|---|---|---|---|---|
| 1,084 | $CH_2$ | H | H | Cl | $X_{13}$ | $SO_2CH_3$ | |
| 1,085 | $CH_2$ | H | H | Cl | $X_{14}$ | $SO_2CH_3$ | |
| 1,086 | $CH_2$ | H | H | Cl | $X_{15}$ | $SO_2CH_3$ | |
| 1,087 | $CH_2$ | H | H | Cl | $X_{16}$ | $SO_2CH_3$ | |
| 1,088 | $CH_2$ | H | H | Cl | $X_{17}$ | $SO_2CH_3$ | |
| 1,089 | $CH_2$ | H | H | Cl | $X_{18}$ | $SO_2CH_3$ | |
| 1,090 | $CH_2$ | H | H | Cl | $X_{19}$ | $SO_2CH_3$ | |
| 1,091 | $CH_2$ | H | H | Cl | $X_{20}$ | $SO_2CH_3$ | |
| 1,092 | $CH_2$ | H | H | Cl | $X_{21}$ | $SO_2CH_3$ | |
| 1,093 | $CH_2$ | H | H | Cl | $X_{22}$ | $SO_2CH_3$ | |
| 1,094 | $CH_2$ | H | H | Cl | $X_{23}$ | $SO_2CH_3$ | |
| 1,095 | $CH_2$ | H | H | Cl | $X_{24}$ | $SO_2CH_3$ | |
| 1,096 | $CH_2$ | H | H | Cl | $X_{25}$ | $SO_2CH_3$ | |
| 1,097 | $CH_2$ | H | H | Cl | $X_{26}$ | $SO_2CH_3$ | |
| 1,098 | $CH_2$ | H | H | Cl | $X_{27}$ | $SO_2CH_3$ | |
| 1,099 | $CH_2$ | H | H | Cl | $X_{28}$ | $SO_2CH_3$ | |
| 1,100 | $CH_2$ | H | H | Cl | $X_{29}$ | $SO_2CH_3$ | |
| 1,101 | $CH_2$ | H | H | Cl | $X_{30}$ | $SO_2CH_3$ | |
| 1,102 | $CH_2$ | H | H | Cl | $X_{31}$ | $SO_2CH_3$ | |
| 1,103 | $CH_2$ | H | H | Cl | $X_{32}$ | $SO_2CH_3$ | |
| 1,104 | $CH_2$ | H | H | Cl | $X_{33}$ | $SO_2CH_3$ | |
| 1,105 | $CH_2$ | H | H | Cl | $X_{34}$ | $SO_2CH_3$ | |
| 1,106 | $CH_2$ | H | H | Cl | $X_{35}$ | $SO_2CH_3$ | |
| 1,107 | $CH_2$ | H | H | Cl | $X_{36}$ | $SO_2CH_3$ | |
| 1,108 | $CH_2$ | H | H | Cl | $X_{37}$ | $SO_2CH_3$ | |
| 1,109 | $CH_2$ | H | H | Cl | $X_{38}$ | $SO_2CH_3$ | |
| 1,110 | $CH_2$ | H | H | Cl | $X_{39}$ | $SO_2CH_3$ | |
| 1,111 | $CH_2$ | H | H | Cl | $X_{40}$ | $SO_2CH_3$ | |
| 1,112 | $CH_2$ | H | H | Cl | $X_{41}$ | $SO_2CH_3$ | |
| 1,113 | $CH_2$ | H | H | Cl | $X_{42}$ | $SO_2CH_3$ | |
| 1,114 | $CH_2$ | H | H | $CH_3$ | $X_1$ | $CF_3$ | |
| 1,115 | $CH_2$ | H | H | $CH_3$ | $X_2$ | $CF_3$ | |
| 1,116 | $CH_2$ | H | H | $CH_3$ | $X_3$ | $CF_3$ | |
| 1,117 | $CH_2$ | H | H | $CH_3$ | $X_4$ | $CF_3$ | |
| 1,118 | $CH_2$ | H | H | $CH_3$ | $X_5$ | $CF_3$ | |
| 1,119 | $CH_2$ | H | H | $CH_3$ | $X_6$ | $CF_3$ | |
| 1,120 | $CH_2$ | H | H | $CH_3$ | $X_7$ | $CF_3$ | |
| 1,121 | $CH_2$ | H | H | $CH_3$ | $X_{10}$ | $CF_3$ | |
| 1,122 | $CH_2$ | H | H | $CH_3$ | $X_{15}$ | $CF_3$ | |
| 1,123 | $CH_2$ | H | H | $CH_3$ | $X_{20}$ | $CF_3$ | |
| 1,124 | $CH_2$ | H | H | $CH_3$ | $X_{21}$ | $CF_3$ | |
| 1,125 | $CH_2$ | H | H | $CH_3$ | $X_{26}$ | $CF_3$ | |
| 1,126 | $CH_2$ | H | H | $CH_3$ | $X_{27}$ | $CF_3$ | |
| 1,127 | $CH_2$ | H | H | $CH_3$ | $X_{29}$ | $CF_3$ | |
| 1,128 | $CH_2$ | H | H | $CH_3$ | $X_{30}$ | $CF_3$ | |
| 1,129 | $CH_2$ | H | H | $CH_3$ | $X_1$ | Br | |
| 1,130 | $CH_2$ | H | H | $CH_3$ | $X_2$ | Br | |
| 1,131 | $CH_2$ | H | H | $CH_3$ | $X_3$ | Br | |
| 1,132 | $CH_2$ | H | H | $CH_3$ | $X_4$ | Br | |
| 1,133 | $CH_2$ | H | H | $CH_3$ | $X_5$ | Br | |
| 1,134 | $CH_2$ | H | H | $CH_3$ | $X_6$ | Br | |
| 1,135 | $CH_2$ | H | H | $CH_3$ | $X_7$ | Br | |
| 1,136 | $CH_2$ | H | H | $CH_3$ | $X_{10}$ | Br | |
| 1,137 | $CH_2$ | H | H | $CH_3$ | $X_{15}$ | Br | |
| 1,138 | $CH_2$ | H | H | $CH_3$ | $X_{20}$ | Br | |
| 1,139 | $CH_2$ | H | H | $CH_3$ | $X_{21}$ | Br | |
| 1,140 | $CH_2$ | H | H | $CH_3$ | $X_{26}$ | Br | |
| 1,141 | $CH_2$ | H | H | $CH_3$ | $X_{27}$ | Br | |
| 1,142 | $CH_2$ | H | H | $CH_3$ | $X_{29}$ | Br | |
| 1,143 | $CH_2$ | H | H | $CH_3$ | $X_{30}$ | Br | |
| 1,144 | $CH_2$ | H | H | $CH_3$ | $X_1$ | CN | |
| 1,145 | $CH_2$ | H | H | $CH_3$ | $X_2$ | CN | |
| 1,146 | $CH_2$ | H | H | $CH_3$ | $X_3$ | CN | |
| 1,147 | $CH_2$ | H | H | $CH_3$ | $X_4$ | CN | |
| 1,148 | $CH_2$ | H | H | $CH_3$ | $X_6$ | CN | |
| 1,149 | $CH_2$ | H | H | $CH_3$ | $X_{10}$ | CN | |
| 1,150 | $CH_2$ | H | H | $CH_3$ | $X_{15}$ | CN | |
| 1,151 | $CH_2$ | H | H | $CH_3$ | $X_{21}$ | CN | |
| 1,152 | $CH_2$ | H | H | $CH_3$ | $X_{26}$ | CN | |
| 1,153 | $CH_2$ | H | H | $CH_3$ | $X_{30}$ | CN | |
| 1,154 | $CH_2$ | H | H | $CF_3$ | $X_1$ | $SO_2CH_3$ | |
| 1,155 | $CH_2$ | H | H | $CF_3$ | $X_2$ | $SO_2CH_3$ | |
| 1,156 | $CH_2$ | H | H | $CF_3$ | $X_3$ | $SO_2CH_3$ | |
| 1,157 | $CH_2$ | H | H | $CF_3$ | $X_4$ | $SO_2CH_3$ | |
| 1,158 | $CH_2$ | H | H | $CF_3$ | $X_6$ | $SO_2CH_3$ | |
| 1,159 | $CH_2$ | H | H | $CF_3$ | $X_{10}$ | $SO_2CH_3$ | |
| 1,160 | $CH_2$ | H | H | $CF_3$ | $X_{15}$ | $SO_2CH_3$ | |
| 1,161 | $CH_2$ | H | H | $CF_3$ | $X_{21}$ | $SO_2CH_3$ | |
| 1,162 | $CH_2$ | H | H | $CF_3$ | $X_{26}$ | $SO_2CH_3$ | |
| 1,163 | $CH_2$ | H | H | $CF_3$ | $X_{30}$ | $SO_2CH_3$ | |
| 1,164 | $CH_3$ | $CH_3$ | $CH_3$ | $CF_3$ | $X_1$ | $SO_2CH_3$ | |
| 1,165 | $CH_3$ | $CH_3$ | $CH_3$ | $CF_3$ | $X_2$ | $SO_2CH_3$ | |
| 1,166 | $CH_3$ | $CH_3$ | $CH_3$ | $CF_3$ | $X_4$ | $SO_2CH_3$ | |
| 1,167 | $CH_3$ | $CH_3$ | $CH_3$ | $CF_3$ | $X_{10}$ | $SO_2CH_3$ | |
| 1,168 | $CH_3$ | $CH_3$ | $CH_3$ | $CF_3$ | $X_{15}$ | $SO_2CH_3$ | |
| 1,169 | $CH_3$ | $CH_3$ | $CH_3$ | $CF_3$ | $X_{21}$ | $SO_2CH_3$ | |
| 1,170 | $CH_3$ | $CH_3$ | $CH_3$ | $CF_3$ | $X_{26}$ | $SO_2CH_3$ | |
| 1,171 | $CH_2$ | H | H | $SO_2CH_3$ | $X_1$ | $CF_3$ | |
| 1,172 | $CH_2$ | H | H | $SO_2CH_3$ | $X_2$ | $CF_3$ | |
| 1,173 | $CH_2$ | H | H | $SO_2CH_3$ | $X_3$ | $CF_3$ | |
| 1,174 | $CH_2$ | H | H | $SO_2CH_3$ | $X_4$ | $CF_3$ | |
| 1,175 | $CH_2$ | H | H | $SO_2CH_3$ | $X_6$ | $CF_3$ | |
| 1,176 | $CH_2$ | H | H | $SO_2CH_3$ | $X_{10}$ | $CF_3$ | |
| 1,177 | $CH_2$ | H | H | $SO_2CH_3$ | $X_{15}$ | $CF_3$ | |
| 1,178 | $CH_2$ | H | H | $SO_2CH_3$ | $X_{21}$ | $CF_3$ | |
| 1,179 | $CH_2$ | H | H | $SO_2CH_3$ | $X_{26}$ | $CF_3$ | |
| 1,180 | $CH_2$ | H | H | $SO_2CH_3$ | $X_{30}$ | $CF_3$ | |
| 1,181 | $CH_2$ | H | H | $CH_3$ | $X_1$ | Cl | |
| 1,182 | $CH_2$ | H | H | $CH_3$ | $X_2$ | Cl | |
| 1,183 | $CH_2$ | H | H | $CH_3$ | $X_3$ | Cl | |
| 1,184 | $CH_2$ | H | H | $CH_3$ | $X_4$ | Cl | |
| 1,185 | $CH_2$ | H | H | $CH_3$ | $X_6$ | Cl | |
| 1,186 | $CH_2$ | H | H | $CH_3$ | $X_{10}$ | Cl | |
| 1,187 | $CH_2$ | H | H | $CH_3$ | $X_{15}$ | Cl | |
| 1,188 | $CH_2$ | H | H | $CH_3$ | $X_{21}$ | Cl | |
| 1,189 | $CH_2$ | H | H | $CH_3$ | $X_{26}$ | Cl | |
| 1,190 | $CH_2$ | H | H | $CH_3$ | $X_{30}$ | Cl | |
| 1,191 | $CH_2$ | H | H | $NO_2$ | $X_1$ | $SO_2CH_3$ | |
| 1,192 | $CH_2$ | H | H | $NO_2$ | $X_2$ | $SO_2CH_3$ | |
| 1,193 | $CH_2$ | H | H | $NO_2$ | $X_4$ | $SO_2CH_3$ | |
| 1,194 | $CH_2$ | H | H | $NO_2$ | $X_{10}$ | $SO_2CH_3$ | |
| 1,195 | $CH_2$ | H | H | $NO_2$ | $X_{15}$ | $SO_2CH_3$ | |
| 1,196 | $CH_2$ | H | H | $NO_2$ | $X_{21}$ | $SO_2CH_3$ | |
| 1,197 | $CH_2$ | H | H | $NO_2$ | $X_{26}$ | $SO_2CH_3$ | |

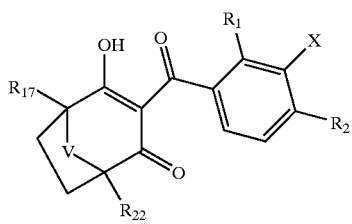

TABLE 2

Compounds of formula (Ib):

$$\text{(Ib)}$$

| Comp. No. | $R_{24}$ | $R_{25}$ | $R_{26}$ | $R_1$ | X | $R_2$ | m.p. (°C.) |
|---|---|---|---|---|---|---|---|
| 2,001 | $CH_3$ | $CH_3$ | $CH_3$ | $CH_3$ | $X_1$ | $SO_2CH_3$ | 157° C. |
| 2,002 | $CH_3$ | $CH_3$ | $CH_3$ | $CH_3$ | $X_2$ | $SO_2CH_3$ | — |
| 2,003 | $CH_3$ | $CH_3$ | $CH_3$ | $CH_3$ | $X_3$ | $SO_2CH_3$ | — |
| 2,004 | $CH_3$ | $CH_3$ | $CH_3$ | $CH_3$ | $X_4$ | $SO_2CH_3$ | — |
| 2,005 | $CH_3$ | $CH_3$ | $CH_3$ | $CH_3$ | $X_5$ | $SO_2CH_3$ | — |
| 2,006 | $CH_3$ | $CH_3$ | $CH_3$ | $CH_3$ | $X_6$ | $SO_2CH_3$ | — |
| 2,007 | $CH_3$ | $CH_3$ | $CH_3$ | $CH_3$ | $X_7$ | $SO_2CH_3$ | — |
| 2,008 | $CH_3$ | $CH_3$ | $CH_3$ | $CH_3$ | $X_8$ | $SO_2CH_3$ | — |
| 2,009 | $CH_3$ | $CH_3$ | $CH_3$ | $CH_3$ | $X_9$ | $SO_2CH_3$ | — |
| 2,010 | $CH_3$ | $CH_3$ | $CH_3$ | $CH_3$ | $X_{10}$ | $SO_2CH_3$ | — |
| 2,011 | $CH_3$ | $CH_3$ | $CH_3$ | $CH_3$ | $X_{11}$ | $SO_2CH_3$ | — |
| 2,012 | $CH_3$ | $CH_3$ | $CH_3$ | $CH_3$ | $X_{12}$ | $SO_2CH_3$ | — |
| 2,013 | $CH_3$ | $CH_3$ | $CH_3$ | $CH_3$ | $X_{13}$ | $SO_2CH_3$ | — |
| 2,014 | $CH_3$ | $CH_3$ | $CH_3$ | $CH_3$ | $X_{14}$ | $SO_2CH_3$ | — |
| 2,015 | $CH_3$ | $CH_3$ | $CH_3$ | $CH_3$ | $X_{15}$ | $SO_2CH_3$ | — |
| 2,016 | $CH_3$ | $CH_3$ | $CH_3$ | $CH_3$ | $X_{16}$ | $SO_2CH_3$ | — |
| 2,017 | $CH_3$ | $CH_3$ | $CH_3$ | $CH_3$ | $X_{17}$ | $SO_2CH_3$ | — |
| 2,018 | $CH_3$ | $CH_3$ | $CH_3$ | $CH_3$ | $X_{18}$ | $SO_2CH_3$ | — |
| 2,019 | $CH_3$ | $CH_3$ | $CH_3$ | $CH_3$ | $X_{19}$ | $SO_2CH_3$ | — |
| 2,020 | $CH_3$ | $CH_3$ | $CH_3$ | $CH_3$ | $X_{20}$ | $SO_2CH_3$ | — |
| 2,021 | $CH_3$ | $CH_3$ | $CH_3$ | $CH_3$ | $X_{21}$ | $SO_2CH_3$ | — |
| 2,022 | $CH_3$ | $CH_3$ | $CH_3$ | $CH_3$ | $X_{22}$ | $SO_2CH_3$ | — |
| 2,023 | $CH_3$ | $CH_3$ | $CH_3$ | $CH_3$ | $X_{23}$ | $SO_2CH_3$ | — |
| 2,024 | $CH_3$ | $CH_3$ | $CH_3$ | $CH_3$ | $X_{24}$ | $SO_2CH_3$ | — |
| 2,025 | $CH_3$ | $CH_3$ | $CH_3$ | $CH_3$ | $X_{25}$ | $SO_2CH_3$ | — |
| 2,026 | $CH_3$ | $CH_3$ | $CH_3$ | $CH_3$ | $X_{26}$ | $SO_2CH_3$ | — |
| 2,027 | $CH_3$ | $CH_3$ | $CH_3$ | $CH_3$ | $X_{27}$ | $SO_2CH_3$ | — |
| 2,028 | $CH_3$ | $CH_3$ | $CH_3$ | $CH_3$ | $X_{28}$ | $SO_2CH_3$ | — |
| 2,029 | $CH_3$ | $CH_3$ | $CH_3$ | $CH_3$ | $X_{29}$ | $SO_2CH_3$ | — |
| 2,030 | $CH_3$ | $CH_3$ | $CH_3$ | $CH_3$ | $X_{30}$ | $SO_2CH_3$ | — |
| 2,031 | $CH_3$ | $CH_3$ | $CH_3$ | $CH_3$ | $X_{31}$ | $SO_2CH_3$ | — |
| 2,032 | $CH_3$ | $CH_3$ | $CH_3$ | $CH_3$ | $X_{32}$ | $SO_2CH_3$ | — |
| 2,033 | $CH_3$ | $CH_3$ | $CH_3$ | $CH_3$ | $X_{33}$ | $SO_2CH_3$ | — |
| 2,034 | $CH_3$ | $CH_3$ | $CH_3$ | $CH_3$ | $X_{34}$ | $SO_2CH_3$ | — |
| 2,035 | $CH_3$ | $CH_3$ | $CH_3$ | $CH_3$ | $X_{35}$ | $SO_2CH_3$ | — |
| 2,036 | $CH_3$ | $CH_3$ | $CH_3$ | $CH_3$ | $X_{36}$ | $SO_2CH_3$ | — |
| 2,037 | $CH_3$ | $CH_3$ | $CH_3$ | $CH_3$ | $X_{37}$ | $SO_2CH_3$ | — |
| 2,038 | $CH_3$ | $CH_3$ | $CH_3$ | $CH_3$ | $X_{38}$ | $SO_2CH_3$ | — |
| 2,039 | $CH_3$ | $CH_3$ | $CH_3$ | $CH_3$ | $X_{39}$ | $SO_2CH_3$ | — |
| 2,040 | $CH_3$ | $CH_3$ | $CH_3$ | $CH_3$ | $X_{40}$ | $SO_2CH_3$ | — |
| 2,041 | $CH_3$ | $CH_3$ | $CH_3$ | $CH_3$ | $X_{41}$ | $SO_2CH_3$ | — |
| 2,042 | $CH_3$ | $CH_3$ | $CH_3$ | $CH_3$ | $X_{42}$ | $SO_2CH_3$ | — |
| 2,043 | $CH_3$ | $CH_3$ | $CH_3$ | Cl | $X_1$ | $SO_2CH_3$ | — |
| 2,044 | $CH_3$ | $CH_3$ | $CH_3$ | Cl | $X_2$ | $SO_2CH_3$ | — |
| 2,045 | $CH_3$ | $CH_3$ | $CH_3$ | Cl | $X_3$ | $SO_2CH_3$ | — |
| 2,046 | $CH_3$ | $CH_3$ | $CH_3$ | Cl | $X_4$ | $SO_2CH_3$ | — |
| 2,047 | $CH_3$ | $CH_3$ | $CH_3$ | Cl | $X_5$ | $SO_2CH_3$ | — |
| 2,048 | $CH_3$ | $CH_3$ | $CH_3$ | Cl | $X_6$ | $SO_2CH_3$ | — |
| 2,049 | $CH_3$ | $CH_3$ | $CH_3$ | Cl | $X_7$ | $SO_2CH_3$ | — |
| 2,050 | $CH_3$ | $CH_3$ | $CH_3$ | Cl | $X_{10}$ | $SO_2CH_3$ | — |
| 2,051 | $CH_3$ | $CH_3$ | $CH_3$ | Cl | $X_{15}$ | $SO_2CH_3$ | — |
| 2,052 | $CH_3$ | $CH_3$ | $CH_3$ | Cl | $X_{20}$ | $SO_2CH_3$ | — |
| 2,053 | $CH_3$ | $CH_3$ | $CH_3$ | Cl | $X_{21}$ | $SO_2CH_3$ | — |
| 2,054 | $CH_3$ | $CH_3$ | $CH_3$ | Cl | $X_{26}$ | $SO_2CH_3$ | — |
| 2,055 | $CH_3$ | $CH_3$ | $CH_3$ | Cl | $X_{27}$ | $SO_2CH_3$ | — |
| 2,056 | $CH_3$ | $CH_3$ | $CH_3$ | Cl | $X_{29}$ | $SO_2CH_3$ | — |
| 2,057 | $CH_3$ | $CH_3$ | $CH_3$ | Cl | $X_{30}$ | $SO_2CH_3$ | — |
| 2,058 | $CH_3$ | $CH_3$ | $CH_3$ | $CH_3$ | $X_1$ | $SCH_3$ | — |
| 2,059 | $CH_3$ | $CH_3$ | $CH_3$ | $CH_3$ | $X_2$ | $SCH_3$ | — |
| 2,060 | $CH_3$ | $CH_3$ | $CH_3$ | $CH_3$ | $X_3$ | $SCH_3$ | — |
| 2,061 | $CH_3$ | $CH_3$ | $CH_3$ | $CH_3$ | $X_4$ | $SCH_3$ | — |
| 2,062 | $CH_3$ | $CH_3$ | $CH_3$ | $CH_3$ | $X_5$ | $SCH_3$ | — |
| 2,063 | $CH_3$ | $CH_3$ | $CH_3$ | $CH_3$ | $X_6$ | $SCH_3$ | — |
| 2,064 | $CH_3$ | $CH_3$ | $CH_3$ | $CH_3$ | $X_7$ | $SCH_3$ | — |
| 2,065 | $CH_3$ | $CH_3$ | $CH_3$ | $CH_3$ | $X_{10}$ | $SCH_3$ | — |
| 2,066 | $CH_3$ | $CH_3$ | $CH_3$ | $CH_3$ | $X_{15}$ | $SCH_3$ | — |
| 2,067 | $CH_3$ | $CH_3$ | $CH_3$ | $CH_3$ | $X_{20}$ | $SCH_3$ | — |
| 2,068 | $CH_3$ | $CH_3$ | $CH_3$ | $CH_3$ | $X_{21}$ | $SCH_3$ | — |
| 2,069 | $CH_3$ | $CH_3$ | $CH_3$ | $CH_3$ | $X_{26}$ | $SCH_3$ | — |
| 2,070 | $CH_3$ | $CH_3$ | $CH_3$ | $CH_3$ | $X_{27}$ | $SCH_3$ | — |
| 2,071 | $CH_3$ | $CH_3$ | $CH_3$ | $CH_3$ | $X_{29}$ | $SCH_3$ | — |
| 2,072 | $CH_3$ | $CH_3$ | $CH_3$ | $CH_3$ | $X_{30}$ | $SCH_3$ | — |
| 2,073 | H | H | $C_2H_5$ | $CH_3$ | $X_1$ | $SO_2CH_3$ | — |
| 2,074 | H | H | $C_2H_5$ | $CH_3$ | $X_2$ | $SO_2CH_3$ | — |
| 2,075 | H | H | $C_2H_5$ | $CH_3$ | $X_4$ | $SO_2CH_3$ | — |
| 2,076 | H | H | $C_2H_5$ | $CH_3$ | $X_{10}$ | $SO_2CH_3$ | — |
| 2,077 | H | H | $C_2H_5$ | $CH_3$ | $X_{15}$ | $SO_2CH_3$ | — |
| 2,078 | H | H | $C_2H_5$ | $CH_3$ | $X_{21}$ | $SO_2CH_3$ | — |
| 2,079 | H | H | $C_2H_5$ | $CH_3$ | $X_{26}$ | $SO_2CH_3$ | — |
| 2,080 | H | H | $C_3H_7$ | $CH_3$ | $X_1$ | $SO_2CH_3$ | — |
| 2,081 | H | H | $C_3H_7$ | $CH_3$ | $X_2$ | $SO_2CH_3$ | — |
| 2,082 | H | H | $C_3H_7$ | $CH_3$ | $X_4$ | $SO_2CH_3$ | — |
| 2,083 | H | H | $C_3H_7$ | $CH_3$ | $X_{10}$ | $SO_2CH_3$ | — |
| 2,084 | H | H | $C_3H_7$ | $CH_3$ | $X_{15}$ | $SO_2CH_3$ | — |
| 2,085 | H | H | $C_3H_7$ | $CH_3$ | $X_{21}$ | $SO_2CH_3$ | — |
| 2,086 | H | H | $C_3H_7$ | $CH_3$ | $X_{26}$ | $SO_2CH_3$ | — |
| 2,087 | $CH_3$ | $CH_3$ | $CH_3$ | Cl | $X_1$ | $SCH_3$ | — |
| 2,088 | $CH_3$ | $CH_3$ | $CH_3$ | Cl | $X_2$ | $SCH_3$ | — |
| 2,089 | $CH_3$ | $CH_3$ | $CH_3$ | Cl | $X_4$ | $SCH_3$ | — |
| 2,090 | $CH_3$ | $CH_3$ | $CH_3$ | Cl | $X_{26}$ | $SCH_3$ | — |
| 2,091 | $CH_3$ | $CH_3$ | $CH_3$ | $CH_3$ | $X_1$ | $CF_3$ | — |
| 2,092 | $CH_3$ | $CH_3$ | $CH_3$ | $CH_3$ | $X_2$ | $CF_3$ | — |
| 2,093 | $CH_3$ | $CH_3$ | $CH_3$ | $CH_3$ | $X_3$ | $CF_3$ | — |
| 2,094 | $CH_3$ | $CH_3$ | $CH_3$ | $CH_3$ | $X_4$ | $CF_3$ | — |
| 2,095 | $CH_3$ | $CH_3$ | $CH_3$ | $CH_3$ | $X_6$ | $CF_3$ | — |
| 2,096 | $CH_3$ | $CH_3$ | $CH_3$ | $CH_3$ | $X_{10}$ | $CF_3$ | — |
| 2,097 | $CH_3$ | $CH_3$ | $CH_3$ | $CH_3$ | $X_{15}$ | $CF_3$ | — |
| 2,098 | $CH_3$ | $CH_3$ | $CH_3$ | $CH_3$ | $X_{21}$ | $CF_3$ | — |
| 2,099 | $CH_3$ | $CH_3$ | $CH_3$ | $CH_3$ | $X_{26}$ | $CF_3$ | — |
| 2,100 | $CH_3$ | $CH_3$ | $CH_3$ | $CH_3$ | $X_{30}$ | $CF_3$ | — |
| 2,101 | $CH_3$ | $CH_3$ | $CH_3$ | $SO_2CH_3$ | $X_1$ | $CF_3$ | — |
| 2,102 | $CH_3$ | $CH_3$ | $CH_3$ | $SO_2CH_3$ | $X_2$ | $CF_3$ | — |
| 2,103 | $CH_3$ | $CH_3$ | $CH_3$ | $SO_2CH_3$ | $X_4$ | $CF_3$ | — |
| 2,104 | $CH_3$ | $CH_3$ | $CH_3$ | $SO_2CH_3$ | $X_{26}$ | $CF_3$ | — |
| 2,105 | $CH_3$ | $CH_3$ | $CH_3$ | $NO_2$ | $X_1$ | $CF_3$ | — |
| 2,106 | $CH_3$ | $CH_3$ | $CH_3$ | $NO_2$ | $X_2$ | $CF_3$ | — |
| 2,107 | $CH_3$ | $CH_3$ | $CH_3$ | $NO_2$ | $X_4$ | $CF_3$ | — |
| 2,108 | $CH_3$ | $CH_3$ | $CH_3$ | $NO_2$ | $X_{26}$ | $CF_3$ | — |
| 2,109 | $CH_3$ | $CH_3$ | $CH_3$ | $NO_2$ | $X_1$ | $SO_2CH_3$ | — |
| 2,110 | $CH_3$ | $CH_3$ | $CH_3$ | $NO_2$ | $X_2$ | $SO_2CH_3$ | — |
| 2,111 | $CH_3$ | $CH_3$ | $CH_3$ | $NO_2$ | $X_4$ | $SO_2CH_3$ | — |
| 2,112 | $CH_3$ | $CH_3$ | $CH_3$ | $NO_2$ | $X_{26}$ | $SO_2CH_3$ | — |
| 2,113 | $CH_3$ | $CH_3$ | $CH_3$ | Br | $X_1$ | $SO_2CH_3$ | — |
| 2,114 | $CH_3$ | $CH_3$ | $CH_3$ | Br | $X_2$ | $SO_2CH_3$ | — |
| 2,115 | $CH_3$ | $CH_3$ | $CH_3$ | Br | $X_4$ | $SO_2CH_3$ | — |
| 2,116 | $CH_3$ | $CH_3$ | $CH_3$ | Br | $X_{26}$ | $SO_2CH_3$ | — |

TABLE 3

Compounds of formula (Ic):

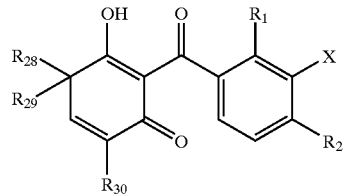

(Ic)

| Comp. No. | $R_{28}$ | $R_{29}$ | $R_{30}$ | $R_1$ | X | $R_2$ | Phys. data |
|---|---|---|---|---|---|---|---|
| 3,001 | $CH_3$ | $CH_3$ | $CH_3$ | $CH_3$ | $X_1$ | $SO_2CH_3$ | — |
| 3,002 | $CH_3$ | $CH_3$ | $CH_3$ | $CH_3$ | $X_2$ | $SO_2CH_3$ | — |
| 3,003 | $CH_3$ | $CH_3$ | $CH_3$ | $CH_3$ | $X_3$ | $SO_2CH_3$ | — |
| 3,004 | $CH_3$ | $CH_3$ | $CH_3$ | $CH_3$ | $X_4$ | $SO_2CH_3$ | — |
| 3,005 | $CH_3$ | $CH_3$ | $CH_3$ | $CH_3$ | $X_5$ | $SO_2CH_3$ | — |
| 3,006 | $CH_3$ | $CH_3$ | $CH_3$ | $CH_3$ | $X_6$ | $SO_2CH_3$ | — |
| 3,007 | $CH_3$ | $CH_3$ | $CH_3$ | $CH_3$ | $X_7$ | $SO_2CH_3$ | — |
| 3,008 | $CH_3$ | $CH_3$ | $CH_3$ | $CH_3$ | $X_8$ | $SO_2CH_3$ | — |
| 3,009 | $CH_3$ | $CH_3$ | $CH_3$ | $CH_3$ | $X_9$ | $SO_2CH_3$ | — |
| 3,010 | $CH_3$ | $CH_3$ | $CH_3$ | $CH_3$ | $X_{10}$ | $SO_2CH_3$ | — |
| 3,011 | $CH_3$ | $CH_3$ | $CH_3$ | $CH_3$ | $X_{11}$ | $SO_2CH_3$ | — |
| 3,012 | $CH_3$ | $CH_3$ | $CH_3$ | $CH_3$ | $X_{12}$ | $SO_2CH_3$ | — |
| 3,013 | $CH_3$ | $CH_3$ | $CH_3$ | $CH_3$ | $X_{13}$ | $SO_2CH_3$ | — |
| 3,014 | $CH_3$ | $CH_3$ | $CH_3$ | $CH_3$ | $X_{14}$ | $SO_2CH_3$ | — |
| 3,015 | $CH_3$ | $CH_3$ | $CH_3$ | $CH_3$ | $X_{15}$ | $SO_2CH_3$ | — |
| 3,016 | $CH_3$ | $CH_3$ | $CH_3$ | $CH_3$ | $X_{16}$ | $SO_2CH_3$ | — |
| 3,017 | $CH_3$ | $CH_3$ | $CH_3$ | $CH_3$ | $X_{17}$ | $SO_2CH_3$ | — |
| 3,018 | $CH_3$ | $CH_3$ | $CH_3$ | $CH_3$ | $X_{18}$ | $SO_2CH_3$ | — |
| 3,019 | $CH_3$ | $CH_3$ | $CH_3$ | $CH_3$ | $X_{19}$ | $SO_2CH_3$ | — |
| 3,020 | $CH_3$ | $CH_3$ | $CH_3$ | $CH_3$ | $X_{20}$ | $SO_2CH_3$ | — |
| 3,021 | $CH_3$ | $CH_3$ | $CH_3$ | $CH_3$ | $X_{21}$ | $SO_2CH_3$ | — |
| 3,022 | $CH_3$ | $CH_3$ | $CH_3$ | $CH_3$ | $X_{22}$ | $SO_2CH_3$ | — |
| 3,023 | $CH_3$ | $CH_3$ | $CH_3$ | $CH_3$ | $X_{23}$ | $SO_2CH_3$ | — |
| 3,024 | $CH_3$ | $CH_3$ | $CH_3$ | $CH_3$ | $X_{24}$ | $SO_2CH_3$ | — |
| 3,025 | $CH_3$ | $CH_3$ | $CH_3$ | $CH_3$ | $X_{25}$ | $SO_2CH_3$ | — |
| 3,026 | $CH_3$ | $CH_3$ | $CH_3$ | $CH_3$ | $X_{26}$ | $SO_2CH_3$ | — |
| 3,027 | $CH_3$ | $CH_3$ | $CH_3$ | $CH_3$ | $X_{27}$ | $SO_2CH_3$ | — |
| 3,028 | $CH_3$ | $CH_3$ | $CH_3$ | $CH_3$ | $X_{28}$ | $SO_2CH_3$ | — |
| 3,029 | $CH_3$ | $CH_3$ | $CH_3$ | $CH_3$ | $X_{29}$ | $SO_2CH_3$ | — |
| 3,030 | $CH_3$ | $CH_3$ | $CH_3$ | $CH_3$ | $X_{30}$ | $SO_2CH_3$ | — |
| 3,031 | $CH_3$ | $CH_3$ | $CH_3$ | $CH_3$ | $X_{31}$ | $SO_2CH_3$ | — |
| 3,032 | $CH_3$ | $CH_3$ | $CH_3$ | $CH_3$ | $X_{32}$ | $SO_2CH_3$ | — |
| 3,033 | $CH_3$ | $CH_3$ | $CH_3$ | $CH_3$ | $X_{33}$ | $SO_2CH_3$ | — |
| 3,034 | $CH_3$ | $CH_3$ | $CH_3$ | $CH_3$ | $X_{34}$ | $SO_2CH_3$ | — |
| 3,035 | $CH_3$ | $CH_3$ | $CH_3$ | $CH_3$ | $X_{35}$ | $SO_2CH_3$ | — |
| 3,036 | $CH_3$ | $CH_3$ | $CH_3$ | $CH_3$ | $X_{36}$ | $SO_2CH_3$ | — |
| 3,037 | $CH_3$ | $CH_3$ | $CH_3$ | $CH_3$ | $X_{37}$ | $SO_2CH_3$ | — |
| 3,038 | $CH_3$ | $CH_3$ | $CH_3$ | $CH_3$ | $X_{38}$ | $SO_2CH_3$ | — |
| 3,039 | $CH_3$ | $CH_3$ | $CH_3$ | $CH_3$ | $X_{39}$ | $SO_2CH_3$ | — |
| 3,040 | $CH_3$ | $CH_3$ | $CH_3$ | $CH_3$ | $X_{40}$ | $SO_2CH_3$ | — |
| 3,041 | $CH_3$ | $CH_3$ | $CH_3$ | $CH_3$ | $X_{41}$ | $SO_2CH_3$ | — |
| 3,042 | $CH_3$ | $CH_3$ | $CH_3$ | $CH_3$ | $X_{42}$ | $SO_2CH_3$ | — |
| 3,043 | $CH_3$ | $CH_3$ | $CH_3$ | $CH_3$ | $X_1$ | $SCH_3$ | — |
| 3,044 | $CH_3$ | $CH_3$ | $CH_3$ | $CH_3$ | $X_2$ | $SCH_3$ | — |
| 3,045 | $CH_3$ | $CH_3$ | $CH_3$ | $CH_3$ | $X_3$ | $SCH_3$ | — |
| 3,046 | $CH_3$ | $CH_3$ | $CH_3$ | $CH_3$ | $X_4$ | $SCH_3$ | — |
| 3,047 | $CH_3$ | $CH_3$ | $CH_3$ | $CH_3$ | $X_5$ | $SCH_3$ | — |
| 3,048 | $CH_3$ | $CH_3$ | $CH_3$ | $CH_3$ | $X_6$ | $SCH_3$ | — |
| 3,049 | $CH_3$ | $CH_3$ | $CH_3$ | $CH_3$ | $X_7$ | $SCH_3$ | — |
| 3,050 | $CH_3$ | $CH_3$ | $CH_3$ | $CH_3$ | $X_{10}$ | $SCH_3$ | — |
| 3,051 | $CH_3$ | $CH_3$ | $CH_3$ | $CH_3$ | $X_{15}$ | $SCH_3$ | — |
| 3,052 | $CH_3$ | $CH_3$ | $CH_3$ | $CH_3$ | $X_{20}$ | $SCH_3$ | — |
| 3,053 | $CH_3$ | $CH_3$ | $CH_3$ | $CH_3$ | $X_{21}$ | $SCH_3$ | — |
| 3,054 | $CH_3$ | $CH_3$ | $CH_3$ | $CH_3$ | $X_{26}$ | $SCH_3$ | — |
| 3,055 | $CH_3$ | $CH_3$ | $CH_3$ | $CH_3$ | $X_{27}$ | $SCH_3$ | — |
| 3,056 | $CH_3$ | $CH_3$ | $CH_3$ | $CH_3$ | $X_{29}$ | $SCH_3$ | — |
| 3,057 | $CH_3$ | $CH_3$ | $CH_3$ | $CH_3$ | $X_{30}$ | $SCH_3$ | — |
| 3,058 | $CH_3$ | $CH_3$ | $CH_3$ | Cl | $X_1$ | $SO_2CH_3$ | — |
| 3,059 | $CH_3$ | $CH_3$ | $CH_3$ | Cl | $X_2$ | $SO_2CH_3$ | — |
| 3,060 | $CH_3$ | $CH_3$ | $CH_3$ | Cl | $X_3$ | $SO_2CH_3$ | — |
| 3,061 | $CH_3$ | $CH_3$ | $CH_3$ | Cl | $X_4$ | $SO_2CH_3$ | — |
| 3,062 | $CH_3$ | $CH_3$ | $CH_3$ | Cl | $X_5$ | $SO_2CH_3$ | — |
| 3,063 | $CH_3$ | $CH_3$ | $CH_3$ | Cl | $X_6$ | $SO_2CH_3$ | — |
| 3,064 | $CH_3$ | $CH_3$ | $CH_3$ | Cl | $X_7$ | $SO_2CH_3$ | — |
| 3,065 | $CH_3$ | $CH_3$ | $CH_3$ | Cl | $X_8$ | $SO_2CH_3$ | — |
| 3,066 | $CH_3$ | $CH_3$ | $CH_3$ | Cl | $X_9$ | $SO_2CH_3$ | — |
| 3,067 | $CH_3$ | $CH_3$ | $CH_3$ | Cl | $X_{10}$ | $SO_2CH_3$ | — |
| 3,068 | $CH_3$ | $CH_3$ | $CH_3$ | Cl | $X_{11}$ | $SO_2CH_3$ | — |
| 3,069 | $CH_3$ | $CH_3$ | $CH_3$ | Cl | $X_{12}$ | $SO_2CH_3$ | — |
| 3,070 | $CH_3$ | $CH_3$ | $CH_3$ | Cl | $X_{13}$ | $SO_2CH_3$ | — |
| 3,071 | $CH_3$ | $CH_3$ | $CH_3$ | Cl | $X_{14}$ | $SO_2CH_3$ | — |
| 3,072 | $CH_3$ | $CH_3$ | $CH_3$ | Cl | $X_{15}$ | $SO_2CH_3$ | — |
| 3,073 | $CH_3$ | $CH_3$ | $CH_3$ | Cl | $X_{16}$ | $SO_2CH_3$ | — |
| 3,074 | $CH_3$ | $CH_3$ | $CH_3$ | Cl | $X_{17}$ | $SO_2CH_3$ | — |
| 3,075 | $CH_3$ | $CH_3$ | $CH_3$ | Cl | $X_{18}$ | $SO_2CH_3$ | — |
| 3,076 | $CH_3$ | $CH_3$ | $CH_3$ | Cl | $X_{19}$ | $SO_2CH_3$ | — |
| 3,077 | $CH_3$ | $CH_3$ | $CH_3$ | Cl | $X_{20}$ | $SO_2CH_3$ | — |
| 3,078 | $CH_3$ | $CH_3$ | $CH_3$ | Cl | $X_{21}$ | $SO_2CH_3$ | — |
| 3,079 | $CH_3$ | $CH_3$ | $CH_3$ | Cl | $X_{22}$ | $SO_2CH_3$ | — |
| 3,080 | $CH_3$ | $CH_3$ | $CH_3$ | Cl | $X_{23}$ | $SO_2CH_3$ | — |
| 3,081 | $CH_3$ | $CH_3$ | $CH_3$ | Cl | $X_{24}$ | $SO_2CH_3$ | — |
| 3,082 | $CH_3$ | $CH_3$ | $CH_3$ | Cl | $X_{25}$ | $SO_2CH_3$ | — |
| 3,083 | $CH_3$ | $CH_3$ | $CH_3$ | Cl | $X_{26}$ | $SO_2CH_3$ | — |
| 3,084 | $CH_3$ | $CH_3$ | $CH_3$ | Cl | $X_{27}$ | $SO_2CH_3$ | — |
| 3,085 | $CH_3$ | $CH_3$ | $CH_3$ | Cl | $X_{28}$ | $SO_2CH_3$ | — |
| 3,086 | $CH_3$ | $CH_3$ | $CH_3$ | Cl | $X_{29}$ | $SO_2CH_3$ | — |
| 3,087 | $CH_3$ | $CH_3$ | $CH_3$ | Cl | $X_{30}$ | $SO_2CH_3$ | — |
| 3,088 | $CH_3$ | $CH_3$ | $CH_3$ | Cl | $X_{31}$ | $SO_2CH_3$ | — |
| 3,089 | $CH_3$ | $CH_3$ | $CH_3$ | Cl | $X_{32}$ | $SO_2CH_3$ | — |
| 3,090 | $CH_3$ | $CH_3$ | $CH_3$ | Cl | $X_{33}$ | $SO_2CH_3$ | — |
| 3,091 | $CH_3$ | $CH_3$ | $CH_3$ | Cl | $X_{34}$ | $SO_2CH_3$ | — |
| 3,092 | $CH_3$ | $CH_3$ | $CH_3$ | Cl | $X_{35}$ | $SO_2CH_3$ | — |
| 3,093 | $CH_3$ | $CH_3$ | $CH_3$ | Cl | $X_{36}$ | $SO_2CH_3$ | — |
| 3,094 | $CH_3$ | $CH_3$ | $CH_3$ | Cl | $X_{37}$ | $SO_2CH_3$ | — |
| 3,095 | $CH_3$ | $CH_3$ | $CH_3$ | Cl | $X_{38}$ | $SO_2CH_3$ | — |
| 3,096 | $CH_3$ | $CH_3$ | $CH_3$ | Cl | $X_{39}$ | $SO_2CH_3$ | — |
| 3,097 | $CH_3$ | $CH_3$ | $CH_3$ | Cl | $X_{40}$ | $SO_2CH_3$ | — |
| 3,098 | $CH_3$ | $CH_3$ | $CH_3$ | Cl | $X_{41}$ | $SO_2CH_3$ | — |
| 3,099 | $CH_3$ | $CH_3$ | $CH_3$ | Cl | $X_{42}$ | $SO_2CH_3$ | — |
| 3,100 | $CH_3$ | $CH_3$ | $CH_3$ | $CH_3$ | $X_1$ | $CF_3$ | — |
| 3,101 | $CH_3$ | $CH_3$ | $CH_3$ | $CH_3$ | $X_2$ | $CF_3$ | — |
| 3,102 | $CH_3$ | $CH_3$ | $CH_3$ | $CH_3$ | $X_3$ | $CF_3$ | — |
| 3,103 | $CH_3$ | $CH_3$ | $CH_3$ | $CH_3$ | $X_4$ | $CF_3$ | — |
| 3,104 | $CH_3$ | $CH_3$ | $CH_3$ | $CH_3$ | $X_6$ | $CF_3$ | — |
| 3,105 | $CH_3$ | $CH_3$ | $CH_3$ | $CH_3$ | $X_{10}$ | $CF_3$ | — |
| 3,106 | $CH_3$ | $CH_3$ | $CH_3$ | $CH_3$ | $X_{15}$ | $CF_3$ | — |
| 3,107 | $CH_3$ | $CH_3$ | $CH_3$ | $CH_3$ | $X_{21}$ | $CF_3$ | — |
| 3,108 | $CH_3$ | $CH_3$ | $CH_3$ | $CH_3$ | $X_{26}$ | $CF_3$ | — |
| 3,109 | $CH_3$ | $CH_3$ | $CH_3$ | $CH_3$ | $X_{30}$ | $CF_3$ | — |
| 3,110 | $CH_3$ | $CH_3$ | $CH_3$ | $NO_2$ | $X_1$ | $SO_2CH_3$ | — |
| 3,111 | $CH_3$ | $CH_3$ | $CH_3$ | $NO_2$ | $X_2$ | $SO_2CH_3$ | — |
| 3,112 | $CH_3$ | $CH_3$ | $CH_3$ | $NO_2$ | $X_4$ | $SO_2CH_3$ | — |
| 3,113 | $CH_3$ | $CH_3$ | $CH_3$ | $NO_2$ | $X_{26}$ | $SO_2CH_3$ | — |
| 3,114 | $CH_3$ | $CH_3$ | $CH_3$ | $NO_2$ | $X_1$ | $CF_3$ | — |
| 3,115 | $CH_3$ | $CH_3$ | $CH_3$ | $NO_2$ | $X_2$ | $CF_3$ | — |
| 3,116 | $CH_3$ | $CH_3$ | $CH_3$ | $NO_2$ | $X_4$ | $CF_3$ | — |
| 3,117 | $CH_3$ | $CH_3$ | $CH_3$ | $NO_2$ | $X_{26}$ | $CF_3$ | — |
| 3,118 | $CH_3$ | $C_2H_5$ | $CH_3$ | $CH_3$ | $X_1$ | $SO_2CH_3$ | — |
| 3,119 | $CH_3$ | $C_2H_5$ | $CH_3$ | $CH_3$ | $X_2$ | $SO_2CH_3$ | — |
| 3,120 | $CH_3$ | $C_2H_5$ | $CH_3$ | $CH_3$ | $X_3$ | $SO_2CH_3$ | — |
| 3,121 | $CH_3$ | $C_2H_5$ | $CH_3$ | $CH_3$ | $X_4$ | $SO_2CH_3$ | — |
| 3,122 | $CH_3$ | $C_2H_5$ | $CH_3$ | $CH_3$ | $X_6$ | $SO_2CH_3$ | — |
| 3,123 | $CH_3$ | $C_2H_5$ | $CH_3$ | $CH_3$ | $X_{10}$ | $SO_2CH_3$ | — |
| 3,124 | $CH_3$ | $C_2H_5$ | $CH_3$ | $CH_3$ | $X_{15}$ | $SO_2CH_3$ | — |

TABLE 3-continued

Compounds of formula (Ic):

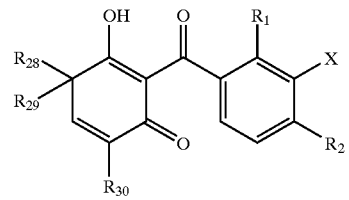

(Ic)

| Comp. No. | $R_{28}$ | $R_{29}$ | $R_{30}$ | $R_1$ | X | $R_2$ | Phys. data |
|---|---|---|---|---|---|---|---|
| 3,125 | $CH_3$ | $C_2H_5$ | $CH_3$ | $CH_3$ | $X_{21}$ | $SO_2CH_3$ | — |
| 3,126 | $CH_3$ | $C_2H_5$ | $CH_3$ | $CH_3$ | $X_{26}$ | $SO_2CH_3$ | — |
| 3,127 | $CH_3$ | $C_2H_5$ | $CH_3$ | $CH_3$ | $X_{30}$ | $SO_2CH_3$ | — |
| 3,128 | $C_2H_5$ | $C_2H_5$ | $CH_3$ | $CH_3$ | $X_1$ | $SO_2CH_3$ | — |
| 3,129 | $C_2H_5$ | $C_2H_5$ | $CH_3$ | $CH_3$ | $X_2$ | $SO_2CH_3$ | — |
| 3,130 | $C_2H_5$ | $C_2H_5$ | $CH_3$ | $CH_3$ | $X_4$ | $SO_2CH_3$ | — |
| 3,131 | $C_2H_5$ | $C_2H_5$ | $CH_3$ | $CH_3$ | $X_{10}$ | $SO_2CH_3$ | — |
| 3,132 | $C_2H_5$ | $C_2H_5$ | $CH_3$ | $CH_3$ | $X_{15}$ | $SO_2CH_3$ | — |
| 3,133 | $C_2H_5$ | $C_2H_5$ | $CH_3$ | $CH_3$ | $X_{21}$ | $SO_2CH_3$ | — |
| 3,134 | $C_2H_5$ | $C_2H_5$ | $CH_3$ | $CH_3$ | $X_{26}$ | $SO_2CH_3$ | — |
| 3,135 | $CH_3$ | $CH_3$ | $CH_3$ | Cl | $X_1$ | $SCH_3$ | — |
| 3,136 | $CH_3$ | $CH_3$ | $CH_3$ | Cl | $X_2$ | $SCH_3$ | — |
| 3,137 | $CH_3$ | $CH_3$ | $CH_3$ | Cl | $X_3$ | $SCH_3$ | — |
| 3,138 | $CH_3$ | $CH_3$ | $CH_3$ | Cl | $X_4$ | $SCH_3$ | — |
| 3,139 | $CH_3$ | $CH_3$ | $CH_3$ | Cl | $X_5$ | $SCH_3$ | — |
| 3,140 | $CH_3$ | $CH_3$ | $CH_3$ | Cl | $X_6$ | $SCH_3$ | — |
| 3,141 | $CH_3$ | $CH_3$ | $CH_3$ | Cl | $X_7$ | $SCH_3$ | — |
| 3,142 | $CH_3$ | $CH_3$ | $CH_3$ | Cl | $X_{10}$ | $SCH_3$ | — |
| 3,143 | $CH_3$ | $CH_3$ | $CH_3$ | Cl | $X_{15}$ | $SCH_3$ | — |
| 3,144 | $CH_3$ | $CH_3$ | $CH_3$ | Cl | $X_{20}$ | $SCH_3$ | — |
| 3,145 | $CH_3$ | $CH_3$ | $CH_3$ | Cl | $X_{21}$ | $SCH_3$ | — |
| 3,146 | $CH_3$ | $CH_3$ | $CH_3$ | Cl | $X_{26}$ | $SCH_3$ | — |
| 3,147 | $CH_3$ | $CH_3$ | $CH_3$ | Cl | $X_{27}$ | $SCH_3$ | — |
| 3,148 | $CH_3$ | $CH_3$ | $CH_3$ | Cl | $X_{29}$ | $SCH_3$ | — |
| 3,149 | $CH_3$ | $CH_3$ | $CH_3$ | Cl | $X_{30}$ | $SCH_3$ | — |

TABLE 4

Compounds of formula (Id):

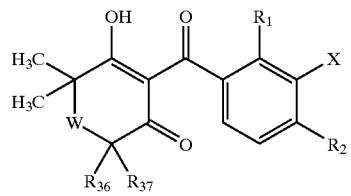

(Id)

| Comp. No. | $R_{36}$ | $R_{37}$ | W | $R_1$ | X | $R_2$ | Phys. data |
|---|---|---|---|---|---|---|---|
| 4,001 | $CH_3$ | $CH_3$ | O | $CH_3$ | $X_1$ | $SO_2CH_3$ | — |
| 4,002 | $CH_3$ | $CH_3$ | O | $CH_3$ | $X_2$ | $SO_2CH_3$ | — |
| 4,003 | $CH_3$ | $CH_3$ | O | $CH_3$ | $X_3$ | $SO_2CH_3$ | — |
| 4,004 | $CH_3$ | $CH_3$ | O | $CH_3$ | $X_4$ | $SO_2CH_3$ | — |
| 4,005 | $CH_3$ | $CH_3$ | O | $CH_3$ | $X_5$ | $SO_2CH_3$ | — |
| 4,006 | $CH_3$ | $CH_3$ | O | $CH_3$ | $X_6$ | $SO_2CH_3$ | — |
| 4,007 | $CH_3$ | $CH_3$ | O | $CH_3$ | $X_7$ | $SO_2CH_3$ | — |
| 4,008 | $CH_3$ | $CH_3$ | O | $CH_3$ | $X_8$ | $SO_2CH_3$ | — |
| 4,009 | $CH_3$ | $CH_3$ | O | $CH_3$ | $X_9$ | $SO_2CH_3$ | — |
| 4,010 | $CH_3$ | $CH_3$ | O | $CH_3$ | $X_{10}$ | $SO_2CH_3$ | — |
| 4,011 | $CH_3$ | $CH_3$ | O | $CH_3$ | $X_{11}$ | $SO_2CH_3$ | — |
| 4,012 | $CH_3$ | $CH_3$ | O | $CH_3$ | $X_{12}$ | $SO_2CH_3$ | — |
| 4,013 | $CH_3$ | $CH_3$ | O | $CH_3$ | $X_{13}$ | $SO_2CH_3$ | — |
| 4,014 | $CH_3$ | $CH_3$ | O | $CH_3$ | $X_{14}$ | $SO_2CH_3$ | — |
| 4,015 | $CH_3$ | $CH_3$ | O | $CH_3$ | $X_{15}$ | $SO_2CH_3$ | — |
| 4,016 | $CH_3$ | $CH_3$ | O | $CH_3$ | $X_{16}$ | $SO_2CH_3$ | — |

TABLE 4-continued

Compounds of formula (Id):

(Id)

| Comp. No. | $R_{36}$ | $R_{37}$ | W | $R_1$ | X | $R_2$ | Phys. data |
|---|---|---|---|---|---|---|---|
| 4,017 | $CH_3$ | $CH_3$ | O | $CH_3$ | $X_{17}$ | $SO_2CH_3$ | — |
| 4,018 | $CH_3$ | $CH_3$ | O | $CH_3$ | $X_{18}$ | $SO_2CH_3$ | — |
| 4,019 | $CH_3$ | $CH_3$ | O | $CH_3$ | $X_{19}$ | $SO_2CH_3$ | — |
| 4,020 | $CH_3$ | $CH_3$ | O | $CH_3$ | $X_{20}$ | $SO_2CH_3$ | — |
| 4,021 | $CH_3$ | $CH_3$ | O | $CH_3$ | $X_{21}$ | $SO_2CH_3$ | — |
| 4,022 | $CH_3$ | $CH_3$ | O | $CH_3$ | $X_{22}$ | $SO_2CH_3$ | — |
| 4,023 | $CH_3$ | $CH_3$ | O | $CH_3$ | $X_{23}$ | $SO_2CH_3$ | — |
| 4,024 | $CH_3$ | $CH_3$ | O | $CH_3$ | $X_{24}$ | $SO_2CH_3$ | — |
| 4,025 | $CH_3$ | $CH_3$ | O | $CH_3$ | $X_{25}$ | $SO_2CH_3$ | — |
| 4,026 | $CH_3$ | $CH_3$ | O | $CH_3$ | $X_{26}$ | $SO_2CH_3$ | — |
| 4,027 | $CH_3$ | $CH_3$ | O | $CH_3$ | $X_{27}$ | $SO_2CH_3$ | — |
| 4,028 | $CH_3$ | $CH_3$ | O | $CH_3$ | $X_{28}$ | $SO_2CH_3$ | — |
| 4,029 | $CH_3$ | $CH_3$ | O | $CH_3$ | $X_{29}$ | $SO_2CH_3$ | — |
| 4,030 | $CH_3$ | $CH_3$ | O | $CH_3$ | $X_{30}$ | $SO_2CH_3$ | — |
| 4,031 | $CH_3$ | $CH_3$ | O | $CH_3$ | $X_{31}$ | $SO_2CH_3$ | — |
| 4,032 | $CH_3$ | $CH_3$ | O | $CH_3$ | $X_{32}$ | $SO_2CH_3$ | — |
| 4,033 | $CH_3$ | $CH_3$ | O | $CH_3$ | $X_{33}$ | $SO_2CH_3$ | — |
| 4,034 | $CH_3$ | $CH_3$ | O | $CH_3$ | $X_{34}$ | $SO_2CH_3$ | — |
| 4,035 | $CH_3$ | $CH_3$ | O | $CH_3$ | $X_{35}$ | $SO_2CH_3$ | — |
| 4,036 | $CH_3$ | $CH_3$ | O | $CH_3$ | $X_{36}$ | $SO_2CH_3$ | — |
| 4,037 | $CH_3$ | $CH_3$ | O | $CH_3$ | $X_{37}$ | $SO_2CH_3$ | — |
| 4,038 | $CH_3$ | $CH_3$ | O | $CH_3$ | $X_{38}$ | $SO_2CH_3$ | — |
| 4,039 | $CH_3$ | $CH_3$ | O | $CH_3$ | $X_{39}$ | $SO_2CH_3$ | — |
| 4,040 | $CH_3$ | $CH_3$ | O | $CH_3$ | $X_{40}$ | $SO_2CH_3$ | — |
| 4,041 | $CH_3$ | $CH_3$ | O | $CH_3$ | $X_{41}$ | $SO_2CH_3$ | — |
| 4,042 | $CH_3$ | $CH_3$ | O | $CH_3$ | $X_{42}$ | $SO_2CH_3$ | — |
| 4,043 | $CH_3$ | $CH_3$ | O | $CH_3$ | $X_1$ | $SCH_3$ | — |
| 4,044 | $CH_3$ | $CH_3$ | O | $CH_3$ | $X_2$ | $SCH_3$ | — |
| 4,045 | $CH_3$ | $CH_3$ | O | $CH_3$ | $X_3$ | $SCH_3$ | — |
| 4,046 | $CH_3$ | $CH_3$ | O | $CH_3$ | $X_4$ | $SCH_3$ | — |
| 4,047 | $CH_3$ | $CH_3$ | O | $CH_3$ | $X_5$ | $SCH_3$ | — |
| 4,048 | $CH_3$ | $CH_3$ | O | $CH_3$ | $X_6$ | $SCH_3$ | — |
| 4,049 | $CH_3$ | $CH_3$ | O | $CH_3$ | $X_7$ | $SCH_3$ | — |
| 4,050 | $CH_3$ | $CH_3$ | O | $CH_3$ | $X_{10}$ | $SCH_3$ | — |
| 4,051 | $CH_3$ | $CH_3$ | O | $CH_3$ | $X_{15}$ | $SCH_3$ | — |
| 4,052 | $CH_3$ | $CH_3$ | O | $CH_3$ | $X_{20}$ | $SCH_3$ | — |
| 4,053 | $CH_3$ | $CH_3$ | O | $CH_3$ | $X_{21}$ | $SCH_3$ | — |
| 4,054 | $CH_3$ | $CH_3$ | O | $CH_3$ | $X_{26}$ | $SCH_3$ | — |
| 4,055 | $CH_3$ | $CH_3$ | O | $CH_3$ | $X_{27}$ | $SCH_3$ | — |
| 4,056 | $CH_3$ | $CH_3$ | O | $CH_3$ | $X_{29}$ | $SCH_3$ | — |
| 4,057 | $CH_3$ | $CH_3$ | O | $CH_3$ | $X_{30}$ | $SCH_3$ | — |
| 4,058 | $CH_3$ | $CH_3$ | O | Cl | $X_1$ | $SO_2CH_3$ | — |
| 4,059 | $CH_3$ | $CH_3$ | O | Cl | $X_2$ | $SO_2CH_3$ | — |
| 4,060 | $CH_3$ | $CH_3$ | O | Cl | $X_3$ | $SO_2CH_3$ | — |
| 4,061 | $CH_3$ | $CH_3$ | O | Cl | $X_4$ | $SO_2CH_3$ | — |
| 4,062 | $CH_3$ | $CH_3$ | O | Cl | $X_5$ | $SO_2CH_3$ | — |
| 4,063 | $CH_3$ | $CH_3$ | O | Cl | $X_6$ | $SO_2CH_3$ | — |
| 4,064 | $CH_3$ | $CH_3$ | O | Cl | $X_7$ | $SO_2CH_3$ | — |
| 4,065 | $CH_3$ | $CH_3$ | O | Cl | $X_8$ | $SO_2CH_3$ | — |
| 4,066 | $CH_3$ | $CH_3$ | O | Cl | $X_9$ | $SO_2CH_3$ | — |
| 4,067 | $CH_3$ | $CH_3$ | O | Cl | $X_{10}$ | $SO_2CH_3$ | — |
| 4,068 | $CH_3$ | $CH_3$ | O | Cl | $X_{11}$ | $SO_2CH_3$ | — |
| 4,069 | $CH_3$ | $CH_3$ | O | Cl | $X_{12}$ | $SO_2CH_3$ | — |
| 4,070 | $CH_3$ | $CH_3$ | O | Cl | $X_{13}$ | $SO_2CH_3$ | — |
| 4,071 | $CH_3$ | $CH_3$ | O | Cl | $X_{14}$ | $SO_2CH_3$ | — |
| 4,072 | $CH_3$ | $CH_3$ | O | Cl | $X_{15}$ | $SO_2CH_3$ | — |
| 4,073 | $CH_3$ | $CH_3$ | O | Cl | $X_{16}$ | $SO_2CH_3$ | — |
| 4,074 | $CH_3$ | $CH_3$ | O | Cl | $X_{17}$ | $SO_2CH_3$ | — |
| 4,075 | $CH_3$ | $CH_3$ | O | Cl | $X_{18}$ | $SO_2CH_3$ | — |
| 4,076 | $CH_3$ | $CH_3$ | O | Cl | $X_{19}$ | $SO_2CH_3$ | — |
| 4,077 | $CH_3$ | $CH_3$ | O | Cl | $X_{20}$ | $SO_2CH_3$ | — |
| 4,078 | $CH_3$ | $CH_3$ | O | Cl | $X_{21}$ | $SO_2CH_3$ | — |

TABLE 4-continued

Compounds of formula (Id):

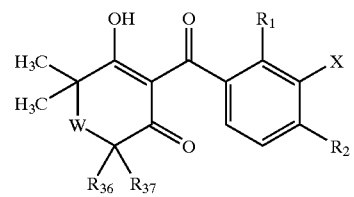

(Id)

| Comp. No. | $R_{36}$ | $R_{37}$ | W | $R_1$ | X | $R_2$ | Phys. data |
|---|---|---|---|---|---|---|---|
| 4,079 | $CH_3$ | $CH_3$ | O | Cl | $X_{22}$ | $SO_2CH_3$ | — |
| 4,080 | $CH_3$ | $CH_3$ | O | Cl | $X_{23}$ | $SO_2CH_3$ | — |
| 4,081 | $CH_3$ | $CH_3$ | O | Cl | $X_{24}$ | $SO_2CH_3$ | — |
| 4,082 | $CH_3$ | $CH_3$ | O | Cl | $X_{25}$ | $SO_2CH_3$ | — |
| 4,083 | $CH_3$ | $CH_3$ | O | Cl | $X_{26}$ | $SO_2CH_3$ | — |
| 4,084 | $CH_3$ | $CH_3$ | O | Cl | $X_{27}$ | $SO_2CH_3$ | — |
| 4,085 | $CH_3$ | $CH_3$ | O | Cl | $X_{28}$ | $SO_2CH_3$ | — |
| 4,086 | $CH_3$ | $CH_3$ | O | Cl | $X_{29}$ | $SO_2CH_3$ | — |
| 4,087 | $CH_3$ | $CH_3$ | O | Cl | $X_{30}$ | $SO_2CH_3$ | — |
| 4,088 | $CH_3$ | $CH_3$ | O | Cl | $X_{31}$ | $SO_2CH_3$ | — |
| 4,089 | $CH_3$ | $CH_3$ | O | Cl | $X_{32}$ | $SO_2CH_3$ | — |
| 4,090 | $CH_3$ | $CH_3$ | O | Cl | $X_{33}$ | $SO_2CH_3$ | — |
| 4,091 | $CH_3$ | $CH_3$ | O | Cl | $X_{34}$ | $SO_2CH_3$ | — |
| 4,092 | $CH_3$ | $CH_3$ | O | Cl | $X_{35}$ | $SO_2CH_3$ | — |
| 4,093 | $CH_3$ | $CH_3$ | O | Cl | $X_{36}$ | $SO_2CH_3$ | — |
| 4,094 | $CH_3$ | $CH_3$ | O | Cl | $X_{37}$ | $SO_2CH_3$ | — |
| 4,095 | $CH_3$ | $CH_3$ | O | Cl | $X_{38}$ | $SO_2CH_3$ | — |
| 4,096 | $CH_3$ | $CH_3$ | O | Cl | $X_{39}$ | $SO_2CH_3$ | — |
| 4,097 | $CH_3$ | $CH_3$ | O | Cl | $X_{40}$ | $SO_2CH_3$ | — |
| 4,098 | $CH_3$ | $CH_3$ | O | Cl | $X_{41}$ | $SO_2CH_3$ | — |
| 4,099 | $CH_3$ | $CH_3$ | O | Cl | $X_{42}$ | $SO_2CH_3$ | — |
| 4,100 | $CH_3$ | $CH_3$ | O | $CH_3$ | $X_1$ | $CF_3$ | — |
| 4,101 | $CH_3$ | $CH_3$ | O | $CH_3$ | $X_2$ | $CF_3$ | — |
| 4,102 | $CH_3$ | $CH_3$ | O | $CH_3$ | $X_3$ | $CF_3$ | — |
| 4,103 | $CH_3$ | $CH_3$ | O | $CH_3$ | $X_4$ | $CF_3$ | — |
| 4,104 | $CH_3$ | $CH_3$ | O | $CH_3$ | $X_6$ | $CF_3$ | — |
| 4,105 | $CH_3$ | $CH_3$ | O | $CH_3$ | $X_{10}$ | $CF_3$ | — |
| 4,106 | $CH_3$ | $CH_3$ | O | $CH_3$ | $X_{15}$ | $CF_3$ | — |
| 4,107 | $CH_3$ | $CH_3$ | O | $CH_3$ | $X_{21}$ | $CF_3$ | — |
| 4,108 | $CH_3$ | $CH_3$ | O | $CH_3$ | $X_{26}$ | $CF_3$ | — |
| 4,109 | $CH_3$ | $CH_3$ | O | $CH_3$ | $X_{30}$ | $CF_3$ | — |
| 4,110 | $CH_3$ | $CH_3$ | O | $NO_2$ | $X_1$ | $SO_2CH_3$ | — |
| 4,111 | $CH_3$ | $CH_3$ | O | $NO_2$ | $X_2$ | $SO_2CH_3$ | — |
| 4,112 | $CH_3$ | $CH_3$ | O | $NO_2$ | $X_4$ | $SO_2CH_3$ | — |
| 4,113 | $CH_3$ | $CH_3$ | O | $NO_2$ | $X_{26}$ | $SO_2CH_3$ | — |
| 4,114 | $CH_3$ | $CH_3$ | O | $NO_2$ | $X_1$ | $CF_3$ | — |
| 4,115 | $CH_3$ | $CH_3$ | O | $NO_2$ | $X_2$ | $CF_3$ | — |
| 4,116 | $CH_3$ | $CH_3$ | O | $NO_2$ | $X_4$ | $CF_3$ | — |
| 4,117 | $CH_3$ | $CH_3$ | O | $NO_2$ | $X_{26}$ | $CF_3$ | — |
| 4,118 | $CH_3$ | $C_2H_5$ | O | $CH_3$ | $X_1$ | $SO_2CH_3$ | — |
| 4,119 | $CH_3$ | $C_2H_5$ | O | $CH_3$ | $X_2$ | $SO_2CH_3$ | — |
| 4,120 | $CH_3$ | $C_2H_5$ | O | $CH_3$ | $X_3$ | $SO_2CH_3$ | — |
| 4,121 | $CH_3$ | $C_2H_5$ | O | $CH_3$ | $X_4$ | $SO_2CH_3$ | — |
| 4,122 | $CH_3$ | $C_2H_5$ | O | $CH_3$ | $X_6$ | $SO_2CH_3$ | — |
| 4,123 | $CH_3$ | $C_2H_5$ | O | $CH_3$ | $X_{10}$ | $SO_2CH_3$ | — |
| 4,124 | $CH_3$ | $C_2H_5$ | O | $CH_3$ | $X_{15}$ | $SO_2CH_3$ | — |
| 4,125 | $CH_3$ | $C_2H_5$ | O | $CH_3$ | $X_{21}$ | $SO_2CH_3$ | — |
| 4,126 | $CH_3$ | $C_2H_5$ | O | $CH_3$ | $X_{26}$ | $SO_2CH_3$ | — |
| 4,127 | $CH_3$ | $C_2H_5$ | O | $CH_3$ | $X_{30}$ | $SO_2CH_3$ | — |
| 4,128 | $C_2H_5$ | $C_2H_5$ | O | $CH_3$ | $X_1$ | $SO_2CH_3$ | — |
| 4,129 | $C_2H_5$ | $C_2H_5$ | O | $CH_3$ | $X_2$ | $SO_2CH_3$ | — |
| 4,130 | $C_2H_5$ | $C_2H_5$ | O | $CH_3$ | $X_4$ | $SO_2CH_3$ | — |
| 4,131 | $C_2H_5$ | $C_2H_5$ | O | $CH_3$ | $X_{10}$ | $SO_2CH_3$ | — |
| 4,132 | $C_2H_5$ | $C_2H_5$ | O | $CH_3$ | $X_{15}$ | $SO_2CH_3$ | — |
| 4,133 | $C_2H_5$ | $C_2H_5$ | O | $CH_3$ | $X_{21}$ | $SO_2CH_3$ | — |
| 4,134 | $C_2H_5$ | $C_2H_5$ | O | $CH_3$ | $X_{26}$ | $SO_2CH_3$ | — |
| 4,135 | $CH_3$ | $CH_3$ | O | Cl | $X_1$ | $SCH_3$ | — |
| 4,136 | $CH_3$ | $CH_3$ | O | Cl | $X_2$ | $SCH_3$ | — |
| 4,137 | $CH_3$ | $CH_3$ | O | Cl | $X_3$ | $SCH_3$ | — |
| 4,138 | $CH_3$ | $CH_3$ | O | Cl | $X_4$ | $SCH_3$ | — |
| 4,139 | $CH_3$ | $CH_3$ | O | Cl | $X_5$ | $SCH_3$ | — |
| 4,140 | $CH_3$ | $CH_3$ | O | Cl | $X_6$ | $SCH_3$ | — |
| 4,141 | $CH_3$ | $CH_3$ | O | Cl | $X_7$ | $SCH_3$ | — |
| 4,142 | $CH_3$ | $CH_3$ | O | Cl | $X_{10}$ | $SCH_3$ | — |
| 4,143 | $CH_3$ | $CH_3$ | O | Cl | $X_{15}$ | $SCH_3$ | — |
| 4,144 | $CH_3$ | $CH_3$ | O | Cl | $X_{20}$ | $SCH_3$ | — |
| 4,145 | $CH_3$ | $CH_3$ | O | Cl | $X_{21}$ | $SCH_3$ | — |
| 4,146 | $CH_3$ | $CH_3$ | O | Cl | $X_{26}$ | $SCH_3$ | — |
| 4,147 | $CH_3$ | $CH_3$ | O | Cl | $X_{27}$ | $SCH_3$ | — |
| 4,148 | $CH_3$ | $CH_3$ | O | Cl | $X_{29}$ | $SCH_3$ | — |
| 4,149 | $CH_3$ | $CH_3$ | O | Cl | $X_{30}$ | $SCH_3$ | — |
| 4,150 | $CH_3$ | $CH_3$ | S | $CH_3$ | $X_1$ | $SO_2CH_3$ | — |
| 4,151 | $CH_3$ | $CH_3$ | S | $CH_3$ | $X_2$ | $SO_2CH_3$ | — |
| 4,152 | $CH_3$ | $CH_3$ | S | $CH_3$ | $X_4$ | $SO_2CH_3$ | — |
| 4,153 | $CH_3$ | $CH_3$ | S | $CH_3$ | $X_{26}$ | $SO_2CH_3$ | — |
| 4,154 | $CH_3$ | $CH_3$ | S | Cl | $X_1$ | $SO_2CH_3$ | — |
| 4,155 | $CH_3$ | $CH_3$ | S | Cl | $X_2$ | $SO_2CH_3$ | — |
| 4,156 | $CH_3$ | $CH_3$ | S | Cl | $X_4$ | $SO_2CH_3$ | — |
| 4,157 | $CH_3$ | $CH_3$ | S | Cl | $X_{26}$ | $SO_2CH_3$ | — |
| 4,158 | $CH_3$ | $CH_3$ | $NCH_3$ | $CH_3$ | $X_1$ | $SO_2CH_3$ | — |
| 4,159 | $CH_3$ | $CH_3$ | $NCH_3$ | $CH_3$ | $X_2$ | $SO_2CH_3$ | — |
| 4,160 | $CH_3$ | $CH_3$ | $NCH_3$ | $CH_3$ | $X_4$ | $SO_2CH_3$ | — |
| 4,161 | $CH_3$ | $CH_3$ | $NCH_3$ | $CH_3$ | $X_{26}$ | $SO_2CH_3$ | — |
| 4,162 | H | H | O | $CH_3$ | $X_1$ | $SO_2CH_3$ | — |
| 4,163 | H | H | O | $CH_3$ | $X_2$ | $SO_2CH_3$ | — |
| 4,164 | H | H | O | $CH_3$ | $X_4$ | $SO_2CH_3$ | — |
| 4,165 | H | H | O | $CH_3$ | $X_{26}$ | $SO_2CH_3$ | — |

Biological Examples

Example B1

Pre-emergent Herbicidal Action

Monocot and dicot test plants are sown in standard soil in plastic pots. Immediately after sowing, the plants are sprayed at a concentration of 2 kg active substance/ha with an aqueous suspension of the test compound [prepared from a 25% wettable powder (Example F3, b) in accordance with WO 97/34485] or an emulsion of the test compound [prepared from a 25% emulsifiable concentrate (Example F1 c)] (500 l of water/ha). The test plants are then cultivated in the greenhouse under optimum conditions. The test is evaluated 3 weeks later on a rating scale of 1–9 (1=total damage, 9=no action). Ratings of 1 to 4 (especially of 1 to 3) denote good to very good herbicidal action.

TABLE B1

Pre-emergent action:

| test plant | Setaria | Cyperus | Sinapsis | Solanig | Stellaria | dosage [g AS/ha] |
|---|---|---|---|---|---|---|
| Active ingredient No. | | | | | | |
| 1,001 | 3 | 3 | 3 | 2 | 2 | 2000 |
| 2,001 | 3 | 3 | 2 | 2 | 2 | 2000 |

The same results are obtained by formulating the compounds of formula I in accordance with Examples F2 and F4 to F8 of WO 97/34485.

Example B2

Post-emergent Herbicidal Action

In a greenhouse, monocot and dicot test plants are sown in standard soil in plastic pots and sprayed in the 4- to 6-leaf stage with an aqueous suspension of the test compounds of formula I prepared from a 25% wettable powder [Example F3, b) of WO 97/34485] or with an emulsion of the test compound of formula I prepared from a 25% emulsifiable concentrate [Example F1 c) of WO 97/34485] at a concentration of 2 kg active substance/ha (500 l of water/ha). The test plants are then further cultivated in the greenhouse under optimum conditions. The test is evaluated about 18 days later on a rating scale of 1–9 (1=total damage, 9=no action). Ratings of 1 to 4 (especially of 1 to 3) denote good to very good herbicidal action. In this test the compounds of formula I exhibit a pronounced herbicidal action.

TABLE B2

| | Post-emergent action: | | | | | |
|---|---|---|---|---|---|---|
| test plant | Setaria | Cyperus | Sinapsis | Solanig | Stellaria | dosage [g AS/ha] |
| Active ingredient No. | | | | | | |
| 1,001 | 2 | 3 | 2 | 2 | 2 | 2000 |
| 2,001 | 3 | 3 | 2 | 2 | 4 | 2000 |

The same results are obtained by formulating the compounds of formula I in accordance with Examples F2 and F4 to F8 of WO 97/34485.

What is claimed is:
1. A compound of formula I

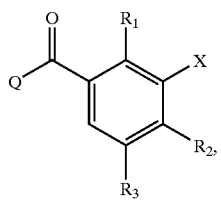

(I)

wherein
X is $L_1$-$Y_1$-$R_4$, $L_2$-$Y_2$-$L_3$-$Y_3$-$R_5$ or $L_4$-$Y_4$-$L_5$-$Y_5$-$L_6$-$Y_6$-$R_6$;

$L_1$, $L_2$, $L_3$, $L_4$, $L_5$, $L_6$, independently of one another, signify $C_1$–$C_6$-alkylene, which may be substituted substituted by $C_1$–$C_4$-alkyl, halogen, $C_1$–$C_4$-alkoxy, $C_2$–$C_6$-alkenyl or $C_2$–$C_6$-alkynyl; or $C_3$–$C_6$-alkenylene, which may be substituted by $C_1$–$C_4$-alkyl, halogen, $C_1$–$C_4$-alkoxy, $C_2$–$C_6$-alkenyl or $C_2$–$C_6$-alkynyl; or $C_3$–$C_6$-alkynylene, which may be substituted by $C_1$–$C_4$-alkyl, halogen, $C_1$–$C_4$-alkoxy, $C_2$–$C_6$-alkenyl or $C_2$–$C_6$-alkynyl;

$Y_1$, $Y_3$, $Y_6$, independently of one another, signify oxygen, sulphur, SO, $SO_2$, $NR_7$, OC(O), $NR_8SO_2$ or $OSO_2$;

$Y_2$, $Y_4$, $Y_5$, independently of one another, signify oxygen, sulphur, SO, $SO_2$, $NR_9$, OC(O) or $NR_{10}SO_2$;

$R_7$, $R_8$, $R_9$ and $R_{10}$, independently of one another, signify hydrogen or $C_1$–$C_6$-alkyl;

$R_1$ and $R_2$, independently of one another, signify halogen, cyano, nitro, amino, $C_1$–$C_6$-alkyl, $C_1$–$C_6$-alkoxy, $C_1$–$C_4$-alkoxy, $C_1$–$C_4$-alkyl, $C_1$–$C_6$-halogenalkyl, $C_2$–$C_6$-alkenyl, $C_2$–$C_6$-alkynyl, $C_1$–$C_6$-alkoxycarbonyl, $C_1$–$C_6$-alkylcarbonyl, $C_1$–$C_6$-alkylthio, $C_1$–$C_6$-alkylsulphinyl, $C_1$–$C_6$-alkylsulphonyl, $C_1$–$C_6$-dialkylaminosulphonyl, $C_1$–$C_6$-alkylaminosulphonyl, $C_1$–$C_4$-alkylsulphonylamino, $C_1$–$C_6$-halogenalkoxy, $OSO_2$—$C_1$–$C_4$-alkyl, $C_1$–$C_6$-halogenalkylthio, $C_1$–$C_6$-halogenalkylsulphinyl, $C_1$–$C_6$-halogenalkylsulphonyl, phenylthio, phenylsulphinyl or phenylsulphonyl;

$R_3$ signifies hydrogen, $C_1$–$C_4$-alkyl or halogen;

$R_4$, $R_5$ and $R_6$, independently of one another, signify hydrogen, $C_1$–$C_6$-alkyl, which may be substituted by the group $A_1$; $C_3$–$C_7$-cycloalkyl, which may be substituted by the group $A_2$; $C_3$–$C_7$-cycloalkyl, which may be interrupted by 1 to 2 oxygen atoms, sulphur or $NR_{11}$; $C_2$–$C_6$-alkenyl, which may be substituted by the group $A_3$; $C_3$–$C_6$-alkynyl, which may be substituted by the group $A_4$; $C_3$–$C_7$-cycloalkyl-$C_1$–$C_4$-alkyl, whereby the cycloalkyl group may be interrupted by 1 to 2 oxygen atoms, sulphur or $NR_{12}$; benzyl or phenyl which may in turn be substituted by halogen, $C_1$–$C_4$-alkyl, $C_1$–$C_4$-alkoxy, $C_1$–$C_4$-halogenalkyl, cyano, nitro, $C_1$–$C_4$-halogenalkoxy, $C_1$–$C_4$-alkylthio, $C_1$–$C_4$-alkylsulphinyl, $C_1$–$C_4$-alkylsulphonyl, $C_1$–$C_4$-dialkylamino, $C_1$–$C_4$-alkylcarbonyl, $C_1$–$C_4$-dialkylaminosulphonyl or $NR_{13}$—CO—$R_{14}$;

$R_{11}$ and $R_{12}$, independently of one another, signify hydrogen or $C_1$–$C_4$-alkyl;

$R_{13}$ and $R_{14}$, independently of one another, signify hydrogen or $C_1$–$C_4$-Alkyl;

$A_1$, $A_2$, $A_3$, $A_4$, independently of one another, are hydroxy, formyl, COOH, $C_1$–$C_6$-alkoxy, $C_1$–$C_4$-alkylthio, $C_1$–$C_4$-alkylsulphinyl, $C_1$–$C_4$-alkylsulphonyl, $OSO_2$—$C_1$–$C_4$-alkyl, $C_1$–$C_6$-alkylamino, $C_1$–$C_6$-dialkylamino, $C_1$–$C_6$-alkylaminocarbonyl, $C_1$–$C_6$-dialkylaminocarbonyl, nitro, halogen, cyano, $C_1$–$C_4$-alkoxyhalogen, $C_1$–$C_4$-alkylcarbonyl, $C_1$–$C_4$-alkoxycarbonyl or phenyl, whereby the phenyl group may in turn be substituted by halogen, $C_1$–$C_4$-alkyl, $C_1$–$C_4$-alkoxy, $C_1$–$C_4$-halogenalkyl, cyano, nitro, $C_1$–$C_4$-halogenalkoxy, $C_1$–$C_4$-alkylthio, $C_1$–$C_4$-alkylsulphinyl, $C_1$–$C_4$-alkylsulphonyl, $C_1$–$C_4$-alkylcarbonyl, $C_1$–$C_4$-dialkylaminosulphonyl or $NR_{15}$—CO—$R_{16}$;

$R_{15}$ and $R_{16}$, independently of one another, signify hydrogen or $C_1$–$C_4$-alkyl;

Q is the group $Q_1$

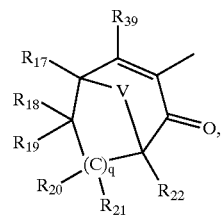

(Q1)

wherein $R_{39}$ signifies hydroxy, halogen, $C_1$–$C_6$-alkoxy, $C_1$–$C_6$-alkylcarbonyloxy, $C_1$–$C_6$-alkoxycarbonyloxy, $C_1$–$C_6$-dialkylamino, COOH, $C_1$–$C_6$-alkenylthio, $C_1$–$C_6$-alkenylsulphinyl, $C_1$–$C_6$-alkenylsulphonyl, $OSO_2$—$C_1$–$C_6$-alkyl, benzoyloxy or $OSO_2$-phenyl, whereby the phenyl and benzoyl groups may in turn be substituted by $C_1$–$C_4$-alkyl, $C_1$–$C_4$-halogenalkyl, $C_1$–$C_4$-alkoxy, $C_1$–$C_4$-halogenalkoxy, $C_1$–$C_4$-alkylcarbonyl, $C_1$–$C_4$-alkoxycarbonyl, halogen, nitro, COOH or cyano; V is $C_1$–$C_4$-alkylene, oxygen, sulphur, SO or $SO_2$;

$R_{17}$, $R_{18}$, $R_{19}$, $R_{20}$, $R_{21}$ and $R_{22}$, independently of one another, signify hydrogen, $C_1$–$C_6$-alkyl, $C_1$–$C_6$-alkoxycarbonyl, $C_2$–$C_6$-alkenyl, $C_2$–$C_6$-alkynyl, $C_1$–$C_6$-alkylthio, $C_1$–$C_6$-alkylsulphinyl, $C_1$–$C_6$-alkylsulphonyl, $C_1$–$C_4$-alkylaminosulphonyl, $C_1$–$C_4$-halogenalkyl, $C_1$–$C_4$-alkylamino, $C_1$–$C_4$-dialkylamino, $C_1$–$C_6$-alkoxy, cyano, nitro, halogen or phenyl, q is 1 or 2; as well as agronomically acceptable salts, isomers and enantiomers of these compounds.

2. A compound according to claim 1, whereby $R_1$ and $R_2$, independently of one another, signify halogen, cyano, nitro, amino, $C_1$–$C_6$-alkyl, $C_1$–$C_6$-alkoxy, $C_1$–$C_4$-alkoxy-$C_1$–$C_4$-alkyl, $C_1$–$C_6$-halogenalkyl, $C_2$–$C_6$-alkenyl, $C_2$–$C_6$-alkynyl, $C_1$–$C_6$-alkoxycarbonyl, $C_1$–$C_6$-alkylcarbonyl, $C_1$–$C_6$-alkylthio, $C_1$–$C_6$-alkylsulphinyl, $C_1$–$C_6$-alkylsulphonyl, $C_1$–$C_6$-dialkylaminosulphonyl, $C_1$–$C_6$-alkylaminosulphonyl, $C_1$–$C_6$-halogenalkoxy, $OSO_2$—$C_1$–$C_4$-alkyl, $C_1$–$C_6$-halogenalkylthio, $C_1$–$C_6$-halogenalkylsulphinyl, $C_1$–$C_6$-halogenalkylsulphonyl, phenylthio, phenylsulphinyl or phenylsulphonyl and $R_{33}$ signifies hydroxy, halogen, $C_1$–$C_6$-alkoxy, $C_1$–$C_6$-alkylcarbonyloxy, $C_1$–$C_6$-alkoxy-carbonyloxy, $C_1$–$C_6$-dialkylamino, COOH, $C_1$–$C_6$-alkylthio, $C_1$–$C_6$-alkylsulphinyl, $C_1$–$C_6$-alkylsulphonyl, $C_1$–$C_4$-alkoxycarbonyl-$C_1$–$C_4$-alkylthio, $C_1$–$C_4$-alkoxycarbonyl-$C_1$–$C_4$-alkylsulphinyl, $C_1$–$C_4$-alkoxycarbonyl-$C_1$–$C_4$-alkylsulphonyl, $C_1$–$C_6$-alkenylthio, $C_1$–$C_6$-alkenylsulphinyl, $C_1$–$C_6$-alkenylsulphonyl, $OSO_2$—$C_1$–$C_6$-alkyl, benzoyloxy, phenylthio, phenylsulphinyl, phenylsulphonyl or $OSO_2$-phenyl, whereby the phenyl and benzoyl groups may in turn be substituted by $C_1$–$C_4$-alkyl, $C_1$–$C_4$-halogenalkyl, $C_1$–$C_4$-alkoxy, $C_1$–$C_4$-halogenalkoxy, $C_1$–$C_4$-alkylcarbonyl, $C_1$–$C_4$-alkoxycarbonyl, halogen, nitro, COOH or cyano.

3. A compound according to claim 1, whereby X is $L_1$-$Y_1$-$R_4$.

4. A compound according to claim 3, whereby $L_1$ signifies methylene.

5. A compound according to claim 1, whereby $R_2$ signifies $C_1$–$C_6$-alkylsulphonyl.

6. A herbicidal and plant growth inhibiting composition, which comprises a herbicidally effective amount of the compound of formula I accordina to claim 1 on an inert carrier.

7. A method of controlling undesirable plant growth, which comprises treating the plants or the locus thereof with a herbicidally effective amount of a compound of formula I according to claim 1 or of a composition containing such a compound.

8. A method of inhibiting undesirable plant growth, which comprises treating the plants or the locus thereof with a herbicidally effective amount of a compound of formula I according to claim 1 or of a composition containing such a compound.

* * * * *